(12) United States Patent
Drager et al.

(10) Patent No.: US 9,707,068 B2
(45) Date of Patent: Jul. 18, 2017

(54) URINARY FLOW CONTROL DEVICE AND METHOD

(71) Applicants: Sam W. Drager, Copley, OH (US); John Bernard Devine, II, Copley, OH (US); Dennis Joseph Dannemiller, Wadsworth, OH (US); Stanley E. Rittgers, Stow, OH (US); Kirby J. Harder, Jr., Copley, OH (US)

(72) Inventors: Sam W. Drager, Copley, OH (US); John Bernard Devine, II, Copley, OH (US); Dennis Joseph Dannemiller, Wadsworth, OH (US); Stanley E. Rittgers, Stow, OH (US); Kirby J. Harder, Jr., Copley, OH (US)

(73) Assignee: 3D UROLOGIC LLC, Copley, OH (US)

( * ) Notice: Subject to any disclaimer, the term of this patent is extended or adjusted under 35 U.S.C. 154(b) by 0 days.

(21) Appl. No.: 14/940,144

(22) Filed: Nov. 12, 2015

(65) Prior Publication Data

US 2016/0135942 A1 May 19, 2016

Related U.S. Application Data

(60) Provisional application No. 62/123,260, filed on Nov. 12, 2014, provisional application No. 62/164,369, filed on May 20, 2015.

(51) Int. Cl.
*A61F 2/00* (2006.01)
*A61F 2/48* (2006.01)

(52) U.S. Cl.
CPC ...... *A61F 2/0036* (2013.01); *A61F 2002/482* (2013.01)

(58) Field of Classification Search
CPC ...... A61F 2/0004; A61F 2/0036; A61F 2/042; A61F 2/0022; A61F 2002/482
See application file for complete search history.

(56) References Cited

U.S. PATENT DOCUMENTS 4,228,550 A * 10/1980 Salkind .................. A61F 2/042
623/23.66
4,976,735 A 12/1990 Griffith
(Continued)

*Primary Examiner* — Christine H Matthews
*Assistant Examiner* — Kaylee Wilson
(74) *Attorney, Agent, or Firm* — D.A. Stauffer Patent Services LLC

(57) ABSTRACT

Device and method for correcting urinary incontinence and urinary retention, by implanting a urinary flow control device for elective user control of urinary function in male and female patients. The device is a mechanical valve for a natural or artificial bladder, and includes a longitudinally extended housing, preferably attached to the abdominal wall. Preferably a bladder anti-prolapse skirt is attached between the bladder and control valve, and the skirt may repair or replace the bladder. The device provides a urine flow channel that passes through the valve from one side to the other of a valve seat where an actuator with a mating stopper is controlled to open and close the valve at the election of the user with an external controller. The valve is an occlusion type, or a pinch type. Preferably the flow channel is an artificial urethra passing through a pinch valve between stopper and valve seat.

14 Claims, 11 Drawing Sheets

(56) References Cited

U.S. PATENT DOCUMENTS

| | | | | |
|---|---|---|---|---|
| 5,634,878 | A * | 6/1997 | Grundei | A61F 2/004 128/DIG. 25 |
| 6,579,225 | B2 * | 6/2003 | Pregenzer | A61F 2/004 600/30 |
| 7,666,133 | B2 | 2/2010 | Drager | |
| 2006/0195009 | A1 * | 8/2006 | Drager | A61F 2/0022 600/30 |
| 2013/0079588 | A1 * | 3/2013 | Crabtree | A61F 2/004 600/31 |

* cited by examiner

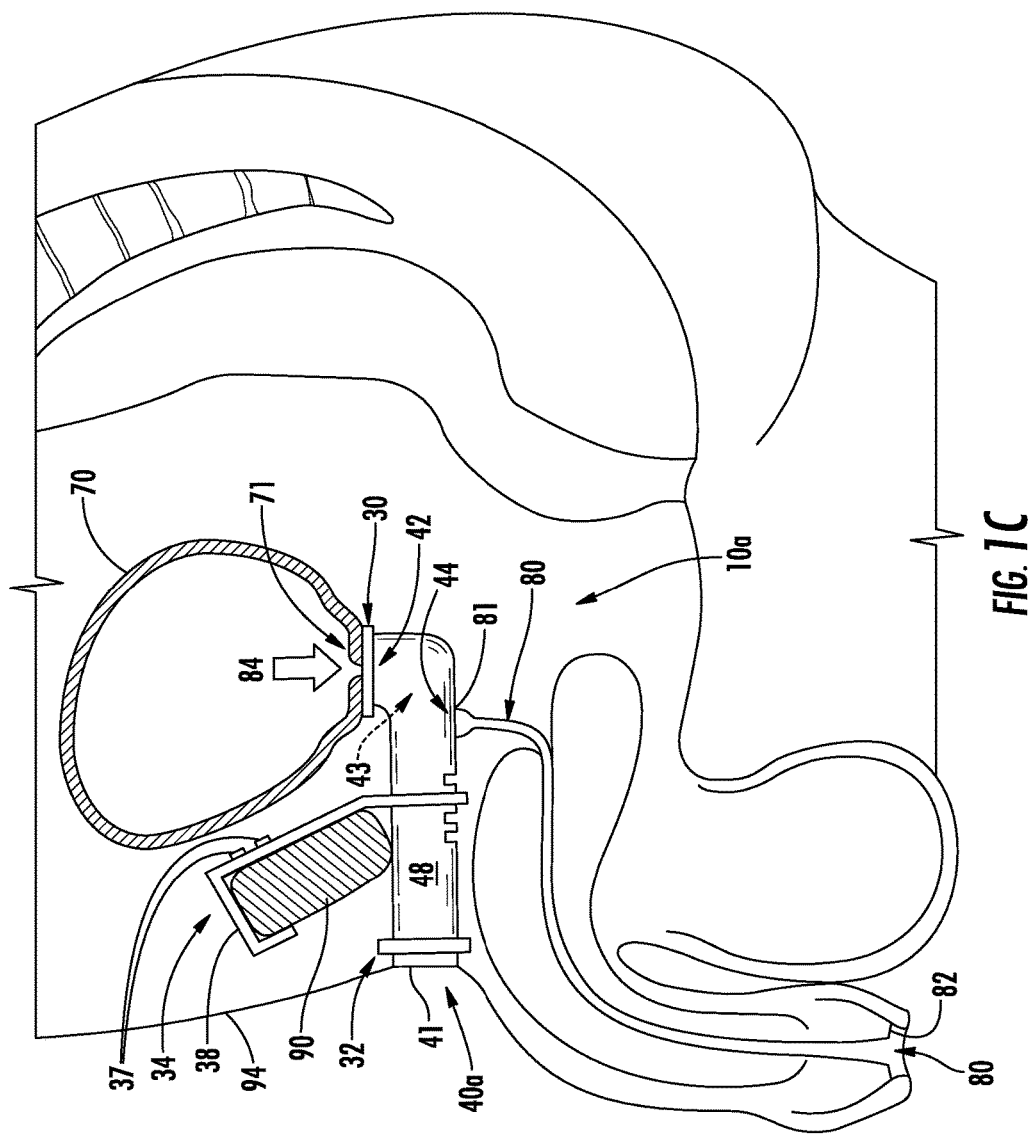

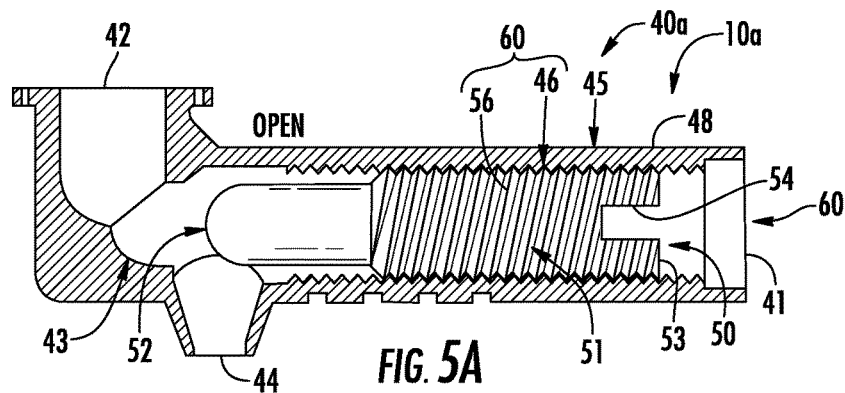
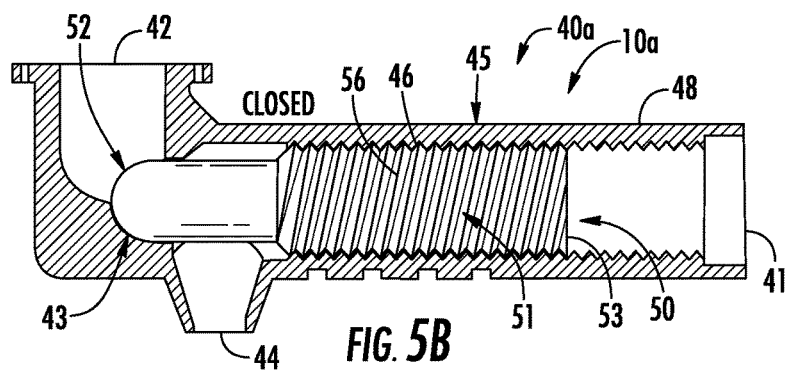
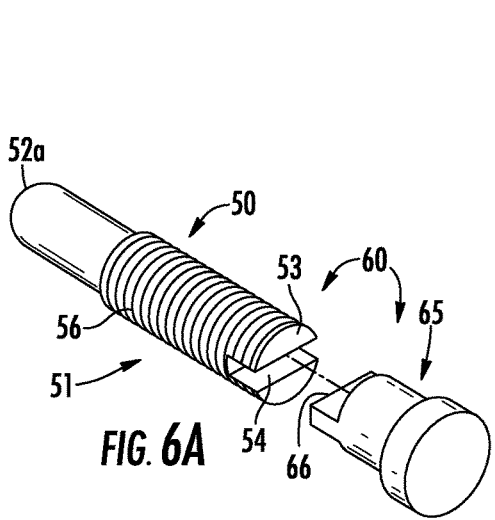
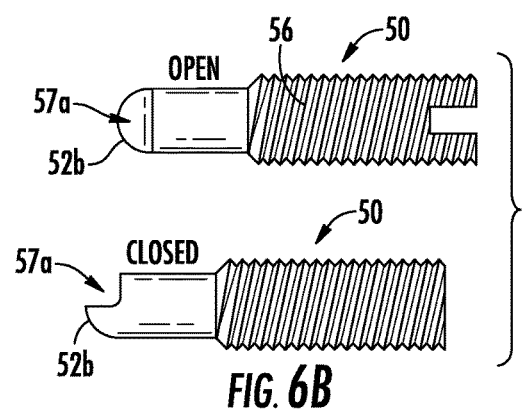
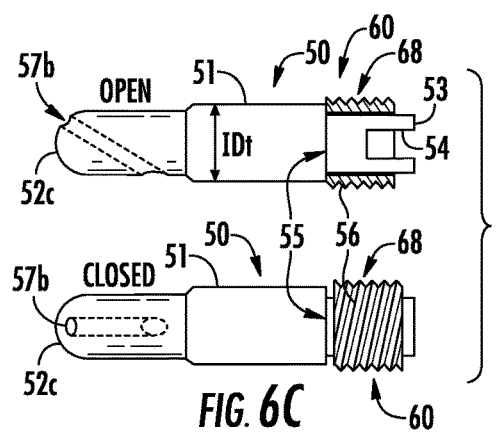

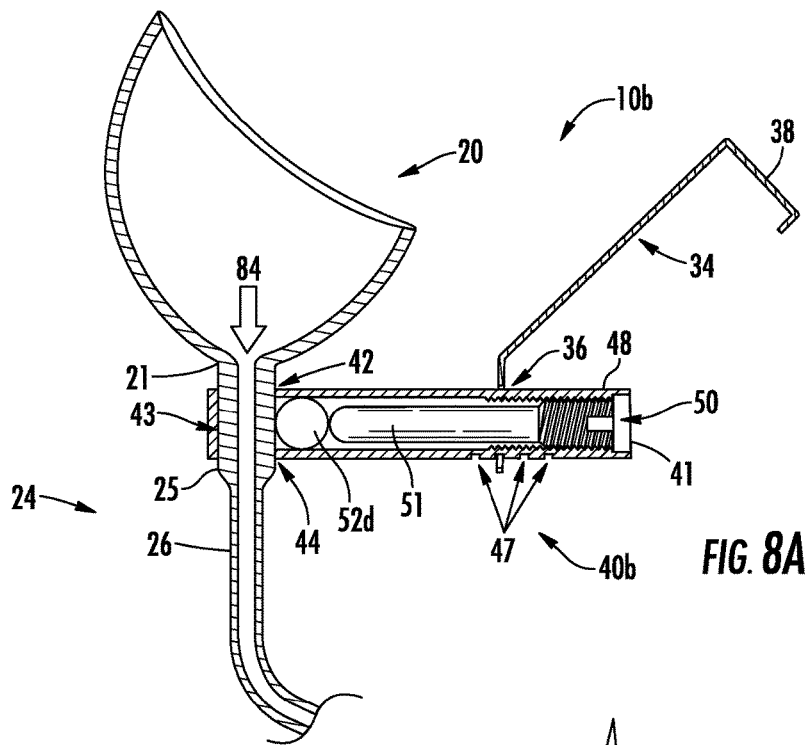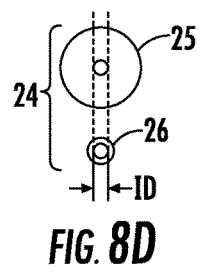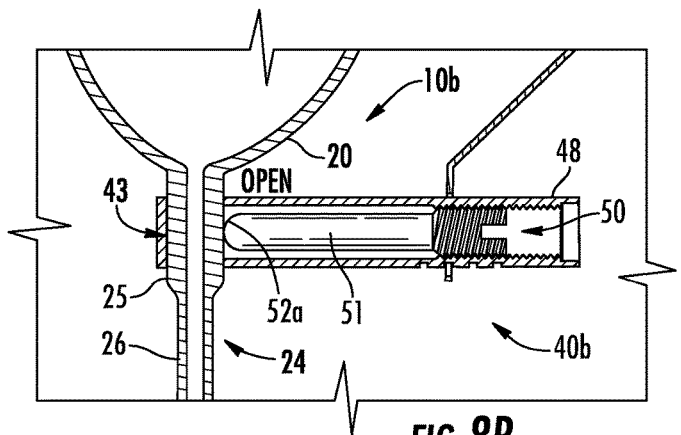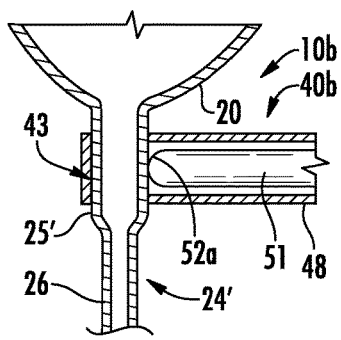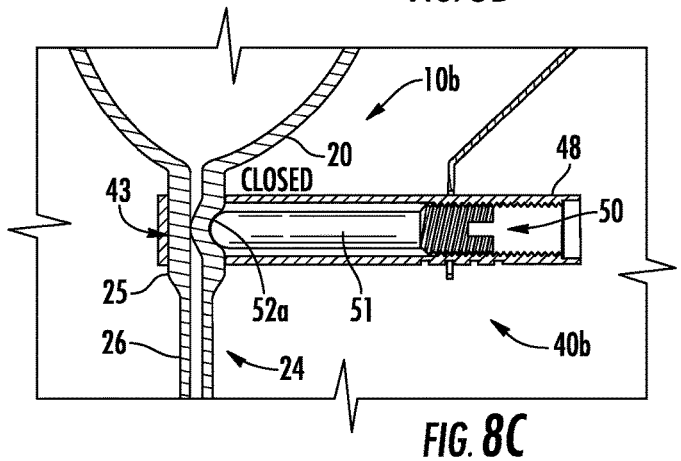

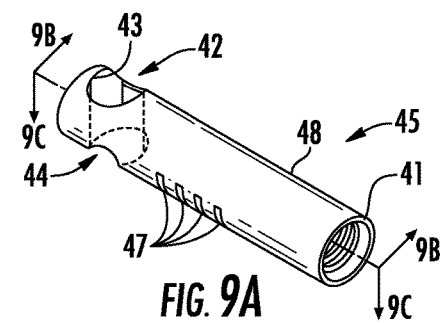
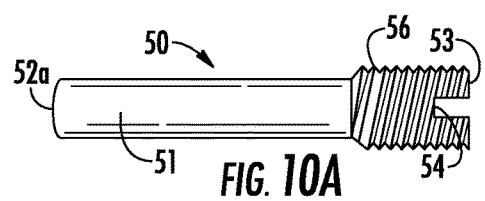
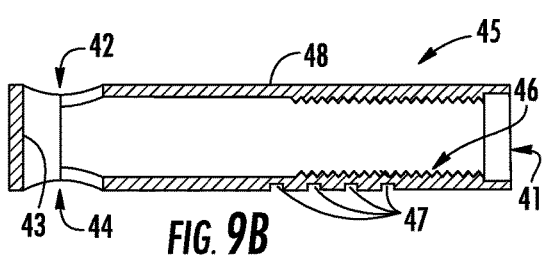
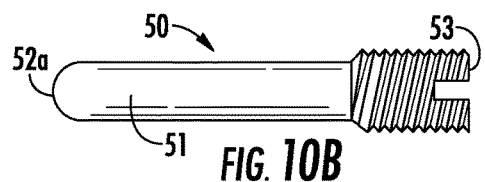
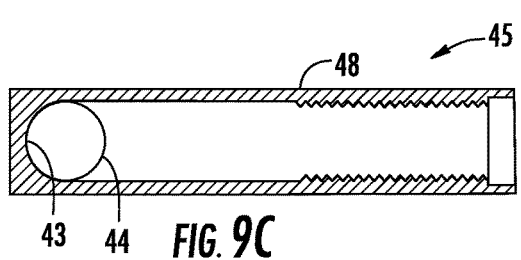
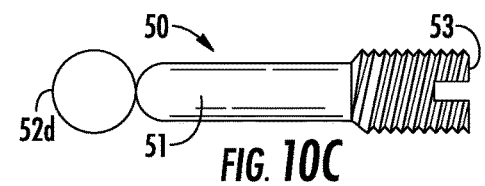
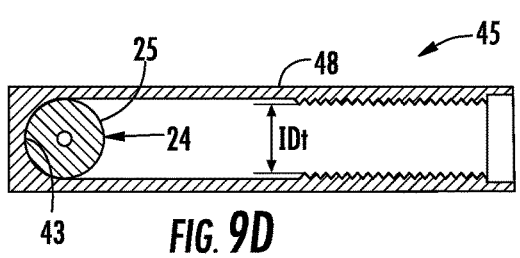
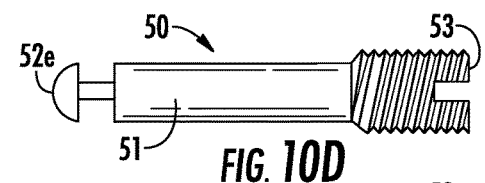
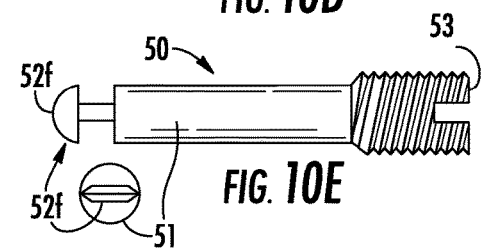
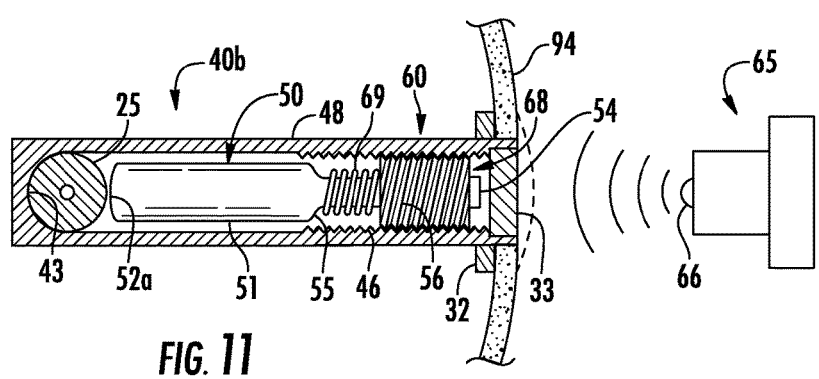

URINARY FLOW CONTROL DEVICE AND METHOD

CROSS-REFERENCE TO RELATED APPLICATIONS

This application claims benefit of priority from U.S. Provisional Patent Applications No. 62/123,260 filed Nov. 12, 2014, and No. 62/164,369 filed May 20, 2015, said applications hereby incorporated in their entirety by reference herein.

This application is related to U.S. Provisional Patent Application No. 61/996,885 filed May 19, 2014, substantial portions of which were materially incorporated in the above-cited May 20, 2015 provisional patent application.

TECHNICAL FIELD OF THE INVENTION

The invention relates to an implantable mechanical device for controlling urine flow, more particularly a urinary flow control valve that is operable on demand from outside the body.

BACKGROUND OF THE INVENTION

The urinary system helps to maintain proper water and salt balance throughout the body. The process of urination begins in the two kidneys, which process fluids and dissolved waste matter to produce urine. Urine flows out of the kidneys into the bladder through two long tubes called ureters. The bladder is a sac that acts as a reservoir for urine. It is covered with a membrane and enclosed in a powerful muscle called the detrusor. The bladder rests on top of the pelvic floor. This is a muscular structure similar to a sling running between the pubic bone in front to the base of the spine. The bladder stores the urine until it is eliminated from the body via a tube called the urethra, which is the lowest part of the urinary tract. (In men it is mostly enclosed in the penis. In women it leads directly out. In either case the urine outlet opening is called the urinary meatus.) The connection between the bladder and the urethra is called the bladder neck (which includes the bladder outlet opening). Strong muscles called sphincter muscles encircle the bladder neck (the smooth internal sphincter muscles) and urethra (the fibrous external sphincter muscles).

The process of urination is a combination of automatic and conscious muscle actions. There are two phases: the emptying phase and the filling and storage phase. When a person has completed urination, the bladder is empty. This triggers the filling and storage phase, which includes both automatic and conscious actions.

An automatic signaling process in the brain uses a pathway of nerve cells and chemical messengers (neurotransmitters) called the cholinergic and adrenergic systems. The brain signals the detrusor muscle, which surrounds the bladder, to relax. As the muscles relax, the bladder expands and allows urine to flow into it from the kidneys. As the bladder fills to its capacity (about 8 to 16 oz of fluid) the nerves in the bladder send back signals of fullness to the spinal cord and the brain.

As the bladder swells, the person becomes conscious of a sensation of fullness. In response, the individual holds the urine back by voluntarily contracting the external sphincter muscles (the muscle group surrounding the urethra). (These are the muscles that children learn to control during the toilet training process.) When the need to urinate overcomes the conscious holding back, then urination (the emptying phase) begins. At the point when a person is ready to urinate, the nervous system initiates the voiding reflex. In this case, the nerves in the spinal cord (not the brain) trigger the event. These nerves signal the detrusor muscles around the bladder to contract. At the same time, nerves are also signaling the involuntary internal sphincter (a strong muscle encircling the bladder neck) to relax. With the bladder muscles squeezing and its neck open, the urine flows out of the bladder into the urethra. Once the urine enters the urethra a person consciously relaxes the external sphincter muscles, which allows urine to pass out. Urine is then completely drained from the bladder and the process of filling and storing begins again.

Urinary Incontinence

In a person with urinary incontinence (UI) the muscles, nerves, or both are no longer under that person's control. This presents the problem of controlling the release and containment of urine. UI affects all aspects of a person's life and may affect their health. Urinary incontinence is an underreported problem estimated to afflict about 25-50 million people in the United States. The annual direct costs (does not include indirect or hidden costs) of providing care for persons with UI is estimated to be in excess of $16 billion (year 1995). Urinary incontinence is one of the most common chronic medical conditions seen in primary care practice. UI is more prevalent than diabetes, Alzheimer's disease, and many other conditions that receive considerably more attention.

Incontinence is an expensive problem, generating more costs each year than coronary artery bypass surgery and renal dialysis combined. Women have higher rates of urinary incontinence than men. Prevalence increases with age, one third of women older than 65 years have some degree of incontinence, and 12 percent have daily incontinence. A shift to a healthier, more active and older population and a society which is increasingly mobile is resulting in an increasing number of persons suffering from incontinence, and a demand from that population for more effective and reliable solutions for urinary incontinence.

Pharmaceutical companies have developed several new incontinence medications. Sales of these medications were predicted to measure billions of dollars in 2004. The market for adult absorbent devices or diapers alone is in excess of $2 billion and continues to grow. Total sales of products used in the diagnosis and treatment of UI were estimated at $1.37 billion in 2001. Due to the size of both current and potential UI markets, medical professionals and product manufacturers have placed significant emphasis on research into the diagnosis and treatment of this condition, which has resulted in the development of several new therapies and approaches that could potentially delay UI symptoms for years in some patients.

UI can affect persons of all ages, and may be the result of physical disability or a psychological condition. There are several different types of incontinence. Acute (or Transient) Incontinence is caused by generally treatable medical problems. Medical conditions such as dehydration, delirium, urinary retention, fecal impaction/constipation, and urinary tract infection; can cause an onset of UI. Additionally, certain medications can cause or contribute to an incontinence problem, such as anticholinergic agents, antihistamines, antidepressants (TCA), phenothiazines, disopyramides, opiates, antispasmodics, Parkinson drugs, alpha-adrenergic agents (high blood pressure drugs), sympathomimetics (decongestants), and sympatholytics (e.g., prazosin, terazosin, and doxazosin).

Chronic UI is conventionally classified into four groups: Stress, Urge, Overflow, and Functional incontinence. They may occur alone or in combination, the latter being more common as the patient ages. Chronic UI is persistent and more difficult problem to treat. Often, more than one type of incontinence is present. Approximately 40% of all incontinence cases fall into more than one of the four categories. A variety of disease and medical problems may contribute to each of the four major types of incontinence. Because incontinence is a symptom rather than a distinct disease, it is often difficult to determine a definite cause.

Stress incontinence is the involuntary leakage of small amounts of urine resulting from an increased pressure in the abdomen. Events which may result in such involuntary leakage include sneezing, coughing, laughing, bending, lifting, etc. While primarily a female problem, men also suffer from stress incontinence. Stress incontinence in men is typically the result of a weakened urethral sphincter that surrounds the urethra, frequently as a result of prostate surgery.

Urge incontinence, characterized by insufficient ability to prevent voiding once the urge to void arises, is most common in middle aged and older people. Detrunorm hyperreflexia or instability which is associated with disorders of the lower urinary tract or neurologic system is a common cause. However, urge incontinence can also be the result of urologic carcinoma, diverticula, or other physical abnormalities.

Overflow incontinence, which accounts for 10-15% of urinary incontinence, is usually the result of an obstruction (e.g., enlarged prostate, urethral stricture) of the bladder outlet or an atonic bladder as the result of neurologic injury (e.g., spinal cord trauma, stroke), diabetic neuropathic bladder, or drug-induced atonia. The obstruction leads to bladder overfilling, resulting in a compulsive detrusor contraction. In this form of UI chronic "dribbling" is common. Drug induced atonia can be caused by anticholinergics, narcotics, anti-depressants, and smooth muscle relaxants.

Functional incontinence accounts for 25% of all incontinence. It occurs primarily when a person is confined and sedentary, such as in a nursing home or during a long period of convalescence. Functional incontinence is sometimes diagnosed as a result of the individual simply being unable to communicate his or her needs, or through other sensory impairments that make the individual unaware of his or her need to void. This condition can further result from decreased mental function, decreased functional status, and/or a simple unwillingness to physically go to the toilet.

UI, or even the fear of an incontinent incidence, can lead to discomfort and embarrassment, and eventually to social withdrawal and isolation. Normal activities, social interaction, and sexual activity are often curtailed or avoided as a result. According to the National Association For Continence, (NAFC), incontinence is the predominant reason aging parents patients are put admitted into nursing homes. Urinary incontinence is a chronic (long-term) problem.

Treatment of Urinary Incontinence

The current protocols for treating urinary incontinence from least to most invasive are education and behavior therapy, pelvic floor muscle exercises, absorbent pads, external devices, medication, non-surgical implants, surgery procedures, and surgical implants.

Pelvic muscle training exercises called Kegel exercises are primarily used to treat people with stress incontinence. However, these exercises may also be beneficial in relieving the symptoms of urge incontinence. The principle behind Kegel exercises is to strengthen the muscles of the pelvic floor, thereby improving the urethral sphincter function. The success of Kegel exercises depends on proper technique and adherence to a regular exercise program. Minimally invasive therapies can lead to improvement in incontinence but not necessarily a cure. Improvement generally does not occur overnight. Patients need time to adapt to behavioral changes. Results with pelvic floor exercises may typically take three to six months.

Diapers and other absorbent constructions are the most popular remedy because they are easily obtained, and can address acute UI symptoms quickly. However, while affording reasonably effective control of urine leakage and providing mobility to the patient, absorbents also have very serious drawbacks. A major deficiency is that urine is not removed from the genital region. The absorbents merely collect and disperse the urine and maintain a moist environment with the urine typically remaining in contact with skin surfaces, causing irritation and discomfort. While improved constructions with different absorbent layers attempt to direct the urine to a region away from the skin and minimize contact, the resulting benefit is less then desired. Absorbent devices also require a large area of absorbent material surrounded by water proof external barriers, usually in the form of pants or diapers. Such an arrangement when dry is uncomfortable to the wearer. When wet the discomfort level increases greatly and the wearer must deal with the distinctive, embarrassing odor of urine. Once removed, whether soiled or not, the disposable-type diaper usually must be disposed of, creating the need to always carry a supply of such absorbent devices.

Catheters

Incontinence treated by catheterization, use of absorbent products, and for males, devices attached to the exterior surface of the penis to collect urine discharge have many disadvantages. Catheterization, whether intermittent or permanent, is an unacceptable approach in many instances and is the least preferred type of incontinence management. The procedure is very inconvenient and many patients are psychologically averse to self-catheterization, or physically unable to perform the manipulations required. Catheters need to be changed frequently. A major deficiency of either permanent or intermittent catheterization is that the urine of virtually every patient becomes contaminated by bacteria. Catheter-associated bacteria or catheter associated urinary tract infection (CAUTI) represent the most common infection acquired in acute care and long-term care facilities. Complications ranging from bladder spasms and catheter leakage to death caused by septicemia are also well known limitations. Bacterial entry into the bladder occurs either from extra luminal migration along the outside of the catheter, contamination on insertion of the catheter, or contamination of the drainage bag, leading to bacterial growth and subsequent migration into the bladder.

The catheter is inserted in and out of the urethra causing a physical manipulation of urethral tissue that may result in scarring, erosion and/or expansion of the urethra, and is generally painful due to nerve endings within it.

Indwelling Catheters are only permitted for insertion up to 30 continuous days, then must be replaced. Indwelling catheters hang from a patient's genitals, thereby interfering with intimacy and sex.

Finally, all types of catheters (indwelling, intermittent, and condom) enable urinary incontinence.

Medications

Pharmaceutical companies have developed several new incontinence medications. Sales of these medications were predicted to measure billions of dollars in 2004. These drugs are useful in treating urge incontinence, but they can have distressing side effects that limit their use, and compliance is poor. Some patients may notice an immediate effect with medical therapy, whereas in others an effect may not be seen for approximately four weeks. Incontinence may also recur after treatment. The disadvantage of medication such as oxybutynin, (including trade names: DETROL® by Pharmacia & Upjohn (now Pfizer), and DITROPAN® by J&J), is the unwanted side effects. Side effects such as dry mouth, nose, and throat, dizziness, drowsiness, and confusion, decreased sweating and skin rash, nausea and constipation, eye pain, and rapid heartbeat.

Surgical Implants

Surgical implant treatments include mid-urethral slings, injection of bulking agents (collagen, etc.) under the bladder neck to provide support, balloons under the bladder neck to provide support, and female urethral inserts. There are nearly 200 procedures for incontinence. Most of these procedures are designed to restore the bladder neck and urethra to their anatomically correct positions in patients with stress incontinence. The American Urological Association suggests that surgery should actually be considered as initial therapy for women with severe stress incontinence. It is an effective and safe alternative when conservative treatments fail. Potential complications of all procedures include obstruction of the outlet from the bladder, causing difficulty in urination and irritation. Another problem with these implants include the fact that bulking agents such as collagen lose their effect and need to be continually reapplied. Some surgical methods such as slings only work in females but are currently a subject of product litigation related to long term effects.

Recent advanced technology implants include electrical nerve stimulation ("e-stim"), and a urethral cuff.

E-stim generally comprises wires carrying electrical pulses from a pacemaker-like stimulator to the bladder sphincter muscles. The wires must be surgically implanted and the stimulator module may be implanted or kept outside the body, in which case medical care is required to prevent infection or damage to the wires where they enter the body. E-stim has limited utility: it only works for urge incontinence, and then provides only about 50% reduction in incontinence. Furthermore, the stimulator may have to be repeatedly reprogrammed as the body becomes less sensitive as it is accustomed to a given level of electrical stimulation. Also, may need to disconnect or remove the device with the onset of Alzheimer's.

The cuff is a hollow tubular sleeve that is surgically positioned around the urethra. An inflatable cushion is inside of the cuff, and a balloon reservoir and pump are interconnected by tubing. The reservoir is implanted in the abdominal cavity, and the pump is placed in a man's scrotum, or subdermally in a woman's lower abdomen. Besides problems positioning the pump in a woman's body where it can be manipulated, it is often prohibitive to implant the cuff due to the very short length of her urethra (e.g., only 1.5-2").

When the pump is hand manipulated the cushion inflates, which compresses the entire perimeter of the natural urethral tissue radially inward. Although intended to work like a sphincter valve, a problem is that it acts on the outside diameter of the urethra (urine conduit), unlike a natural sphincter which is included in the tissue of the urine conduit, so that it closes by making elastic changes in the conduit walls, i.e., deforming itself to reduce its inside diameter to essentially zero. On the other hand, the cuffs radial compression applied to the outside diameter of the urethra/conduit must change the conduit wall to a smaller circumference (a smaller annular volume), which means that some of the tissue mass must be moved out of the way, e.g., by radial compaction into a smaller volume and/or by longitudinal extrusion and/or by wrinkling the ID. The urethra itself is not designed to do any of those things, therefor it is traumatized whenever it is compressed by the cuff, which is most of the time except when voiding. Furthermore, the urethra is living tissue which needs blood circulation that may be restricted by the outside compression. And if the cuff ID wrinkles when compressed, then that creates a wrinkled ID surface which is may abrade and/or pinch the urethra surface. Finally, the longer the cuff compression zone is, the worse the trauma to the urethra tissue may be (because annular volume is proportional to length).

Other problems common with the cuff include: bladder neck and scrotum erosion and ischemic injury; disconnection or migration of the components; pressurizing fluid leakage or breakage of the components; may need to disconnect/disable or remove the device with the onset of Alzheimer's. Also, implantation of the cuff requires several invasive surgeries over the course of about 12 weeks: implant components, let swelling go down, hook up components via surgery, let swelling go down, then activate the device.

Bladder Replacement and Urinary Diversion Surgeries

The abovedescribed implants are designed to improve function of an existing bladder, however incontinence must also be dealt with when the bladder (with sphincters) is surgically removed (aka cystectomy), such as may be necessary due to, for example, bladder cancer, injury/abdominal wounds, and other types of bladder destruction. In such cases, urinary diversion and/or surgical bladder replacement/reconstruction are the remaining options presently available. Other current surgical methods offer only temporary solutions.

A urostomy is a surgical procedure that creates a stoma (artificial opening) for draining the urinary system by diversion of the urine flow. A urostomy may be used for temporary urinary diversion in cases where drainage of urine through the bladder and/or urethra is not possible, e.g. after extensive surgery or in case of obstruction; however a urostomy is most commonly performed after cystectomy (bladder removal).

The three main types of urinary diversion surgeries suitable for use after cystectomy are ileal conduit, Indiana pouch reservoir and orthotopic neobladder.

With the ileal conduit, the ureters drain freely into part of the ileum (the last segment of the small intestines) and urine is brought out through an opening, called a stoma, in the abdominal wall and an external bag gathers urine as it drains from the ileal conduit.

The Indiana pouch is made out of portions of the large intestine, so no urine collection bags are needed, but a catheter must be passed through the stoma and into the pouch to empty urine.

The neobladder (a.k.a. "continent urostomy") is a tissue construct replacement bladder formed out of a transplanted segment of small bowel (intestines). The small bowel tissue is surgically formed into a bladder-like reservoir (or "pouch") which is connected between the ureters and the urethra, and then urine is evacuated via a catheter inserted into the urethra to empty it (since the bladder sphincter is gone). This technique avoids the need for a stoma bag on a urostomy, but instead presents the infection and other problems caused by catheter use.

These urinary diversion procedures have disadvantages and adverse effects such as osteoporosis and bowel tissue absorbance of urine and catheters inserted into stoma to void urine can introduce bacteria into the body leading to infections. Current orthotopic neobladder procedures that make use of intestinal cells cause the body to absorb osteoporosis-causing calcium and other substances that a normal bladder eliminates from the body. Despite its adverse effects and limitations, the use of bowel segments remains the gold standard as of today.

A prior art implantable bladder replacement device by Griffith, U.S. Pat. No. 4,976,735 (issued 1990) includes a prosthetic bladder that doesn't collapse when drained, therefor it requires an air vent through the body of the patient. The vent creates problems related to contamination and leakage.

In an effort to find an alternative to use of bowel segments in his pediatric surgical practice—as there was a shortage of organs (in this case bladders) and not enough donors to meet the high demand—Dr. Anthony Atala began research in 1990 on how to successfully create and implant a functioning artificial bladder grown from autologous human cells (urothelial and smooth muscle cells from the receiving patient) via a tissue engineering approach. Problems with Atala's and others' tissue engineered artificial bladders or constructs are that: autologous cells must be cancer free; there is a lack of sufficient nerve conductivity and blood flow; and the inability to create a functional valve construct to make the artificial bladder fully functional on its own. Thus with an artificial bladder or construct patients must still empty their bladders regularly with a catheter. A functional valve construct could make this a viable solution.

Clinicians who work daily with patients with severe bladder dysfunction, UI and retention issues, know and appreciate the importance of having technologies to assist in improving their patients' overall health by mitigating existing conditions; thus resetting the patients for their return to work, duty, and daily life. Currently there is a subset of patients for whom clinicians have limited or even no options other than a urethral catheter and being placed in an institution to be cared for as family becomes overwhelmed with their care issues.

Urinary incontinence affects the quality of life for all those who are afflicted with it, or who care for them. The current methods of treatment do not provide adequate remedies or treatments for urinary incontinence, and all introduce extra problems ranging from life limiting inconvenience to infections that can even be life threatening. Therefor it is an object of the present invention to provide a device and method that remedies urinary incontinence while overcoming the problems and limitations of current methods such as those described above, thereby significantly improving quality of life for the users.

BRIEF SUMMARY OF THE INVENTION

According to the invention, an implantable urinary flow control device for elective user control of urinary function in male and female patients includes: a control valve adapted for implantation in a urine flow channel that conducts urine from a bladder to a urine outlet opening, wherein the control valve comprises: a generally tubular, longitudinally extending valve housing comprising a valve seat at a proximal and, and a control portal at a distal end; and an operationally moveable valve actuator extending longitudinally within the housing, and comprising a stem with a stopper at a proximal valve seat end, and an actuator driving mechanism associated therewith; and a separate external valve control tool adapted to operationally engage with the actuator driving mechanism for elective user control of operational movement of the actuator between open and closed positions, wherein the closed position prevents urine flow through the valve seat by engaging the stopper with the valve seat, and the open position allows urine to flow through the valve seat by disengaging the stopper; and the control valve adaptation for implantation includes: a valve inlet that directs the urine flow channel from the bladder to the valve seat, and a valve outlet that directs the urine flow channel from the valve seat to the urine outlet opening.

Other features according to the invention may include:
bladder skirt
   partial=bladder anti-prolapse support
   full=artificial bladder/replacement
housing attached to pubic synthesis
tube operational end is transcutaneous
   or subcutaneous (e.g., using a motor, magnetic effects, etc.)
valve actuator is threaded to match internal thread of housing tube (optional)
valve turned by an actuator control tool (optionally by a motor)
Valve is One of Following Types:
   occlusion type, wherein valve parts are immersed in the urine=¼ turn to align flow passage through stopper like a ball valve or stopper is advanced to fill valve seat
   pinch type, wherein the urine passes through the valve while completely contained in a tubular duct, i.e., an artificial urethra preferably made of silicone rubber (SR), that extends between the valve stopper and the valve seat. Flow is stopped by pinching the duct closed by advancing the stopper into the seat.

In the pinch valve design, the artificial urethra (SR tube) replaces the natural urethra from bladder to urethral meatus (attached at meatus and sleeved inside any portion of urethra that is embedded in tissue, e.g., inside penis.)

According to the invention an incontinence correction method comprises replacing partial or complete bladder, sphincter valve, and urethra with artificial substitutes, wherein the artificial sphincter valve is a mechanical valve that transversely pinches a resilient urine duct (artificial urethra) to close, and releases pinch force to allow duct to open for draining of bladder by gravity and/or by pressure from detrusor muscles if present and functional.

Note advantageous straight through passage without stone producing nindi.

According to the invention an incontinence correction method alternatively comprises the combination of our valve system with a tissue engineered or regenerative bladder construct.

Our device addresses the existing "gaps" in restorative treatments and provides a much needed modality that would be a significant improvement over what clinicians can currently offer their most challenging patients, due to the limitations and rates of failures of existing devices. Our device and method addresses the shortcomings of tissue engineered, and artificial bladders, and other incontinence medical devices. Also, this device will significantly improve the overall health of patients and thus reduce medical care costs associated with hospitalization and continued institutionalization for incontinence care.

There are currently three primary medical device treatment approaches available to clinicians. Indicated below are the advantages of using our device versus current market alternatives: catheter (C), cuff (F), and e-stim (E) modalities:
   May be a completely mechanical device. F and E are not.
   We implant a valve that does not act upon the natural urethra. C and F both traumatize the urethra and cause erosion (F by squeezing, and C by repeated sliding inside it.)
   We work with any kind of bladder: complete or partial or removed, natural or artificial, tissue construct, etc. E needs nerve conductivity of the bladder to create continence. C and F need a complete bladder equivalent which may mean extra surgery to provide.

No battery needed. E needs one so surgical replacement operations (reops) are necessary over time.

Can be used in cancer patients, E cannot.

Does not promote urinary tract infection (UTI), C does.

Anticipated complete elimination of urinary incontinence (UI), making 100% dryness the new benchmark, whereas C, F and E fail to achieve and maintain 100% continence;

Patient can void on demand by opening the valve, and regain continence by closing valve. E does not work on demand;

Patient enabled to void naturally via urethra or a permanently implanted substitute. C involves relatively difficult and potentially painful insertion and removal of a foreign body.

Caregiver can apply modesty shielding to operate our device and still maintain patient's self dignity. C and F require seeing and touching genitalia when used.

Causation neutral (does not matter why patient is incontinent). F and E are causation specific.

Implantation of our device is expected to eliminate any stage of UI (i.e. light, moderate or severe). F and E cannot.

Patient may remain sexually active. Those with indwelling C cannot.

One surgery for implantation and activation of full function. F and E require multiple surgeries.

Portal through the abdomen permits access to the interior of the valve for maintenance without surgical intervention, F and E do not.

Portal and/or artificial urine duct enable clinician to inspect patient's urinary system with flexible endoscope and/or other devices any time after implantation. F and E do not.

Device is a substantially closed system, thus reducing risk of urinary tract infections (portal through skin is relatively simple to care for with well known protocols for infection avoidance). C creates chronic exposure to infections.

Viable alternative for patients with prior bladder diversion surgery and/or when natural bladder is removed or has been destroyed by trauma, by providing an entire artificial bladder system comprised of bladder, valve, and urethra to control urine flow. C, F and E cannot.

With our artificial urine duct sleeved in, and/or substituted for the natural urethra, a scopic or medicinal medical device can be inserted into the urinary tract without causing pain to the patient (only a feeling of pressure).

The present invention overcomes at least one disadvantage identified in the prior art by providing a urinary bladder valve assembly adapted for implantation into a male or female patient having a natural bladder, portion of natural bladder, bladder destroyed by trauma, alloplastic bladder, neoplast bladder, bladder reconstruction, or prior bladder\urinary diversion surgery or any other natural or artificial bladder of a patient or any combination thereof.

More about the Pinch Valve:

larger OD tubing in the valve thicker wall optional in the valve low Durometer except for a tougher skin, higher Durometer surface stopper curved like the seat stopper connection to actuator is adapted for disassociating axial rotation from longitudinal movement caused by operation of the valve actuator one or more restriction bumps protruding laterally from the valve seat one or more restriction bumps protruding inward from inside surface of tubing Skirt:

provide a skirt big enough to replace the bladder, and surgeon can cut to size he wants, then stitch to the bladder.

skirt can be modified by adding SR material.

Other objects, features and advantages of the invention will become apparent in light of the following description thereof.

BRIEF DESCRIPTION OF THE DRAWINGS

Reference will be made in detail to preferred embodiments of the invention, examples of which are illustrated in the accompanying drawing figures. The figures are intended to be illustrative, not limiting. Although the invention is generally described in the context of these preferred embodiments, it should be understood that it is not intended to limit the spirit and scope of the invention to these particular embodiments.

Certain elements in selected ones of the drawings may be illustrated not-to-scale, for illustrative clarity. The cross-sectional views, if any, presented herein may be in the form of "slices", or "near-sighted" cross-sectional views, omitting certain background lines which would otherwise be visible in a true cross-sectional view, for illustrative clarity.

Elements of the figures can be numbered such that similar (including identical) elements may be referred to with similar numbers in a single drawing. For example, each of a plurality of elements collectively referred to as 199 may be referred to individually as 199*a*, 199*b*, 199*c*, etc. Or, related but modified elements may have the same number but are distinguished by primes. For example, 109, 109', and 109" are three different versions of an element 109 which are similar or related in some way but are separately referenced for the purpose of describing modifications to the parent element (109). Such relationships, if any, between similar elements in the same or different figures will become apparent throughout the specification, including, if applicable, in the claims and abstract.

Figure 1A:
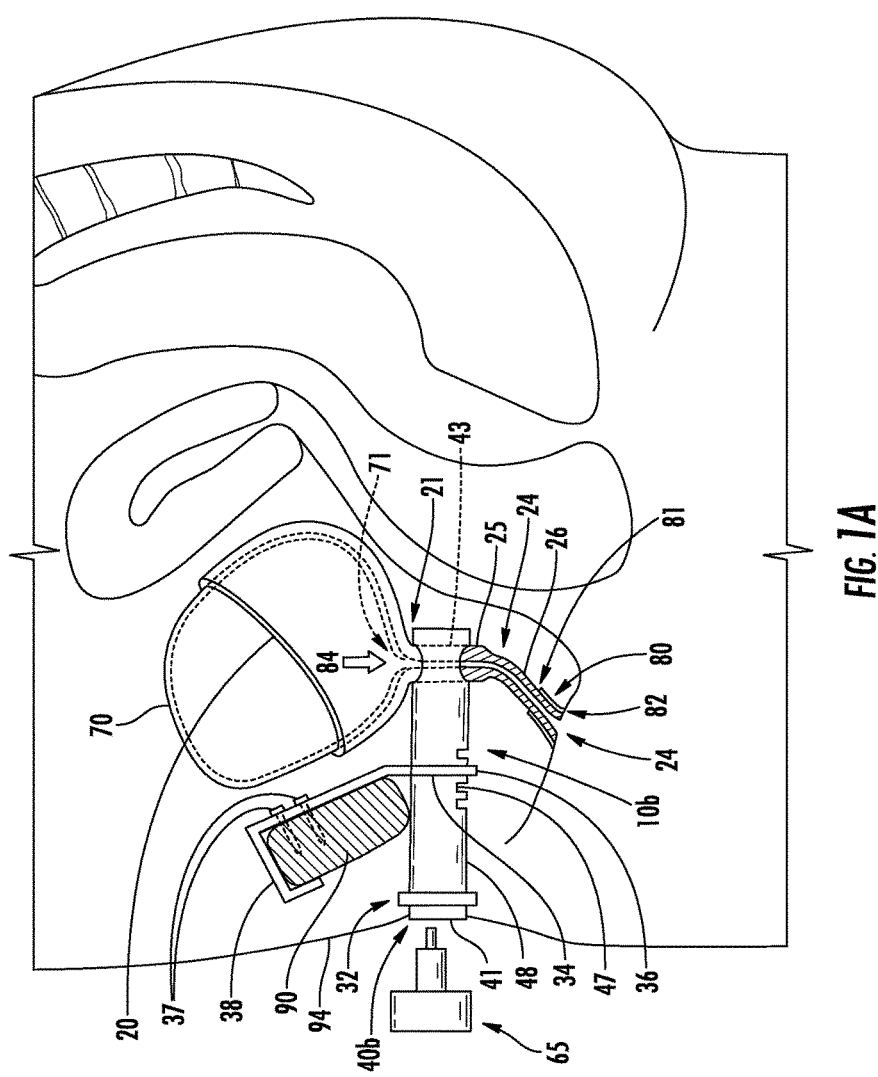
Figure 1B:
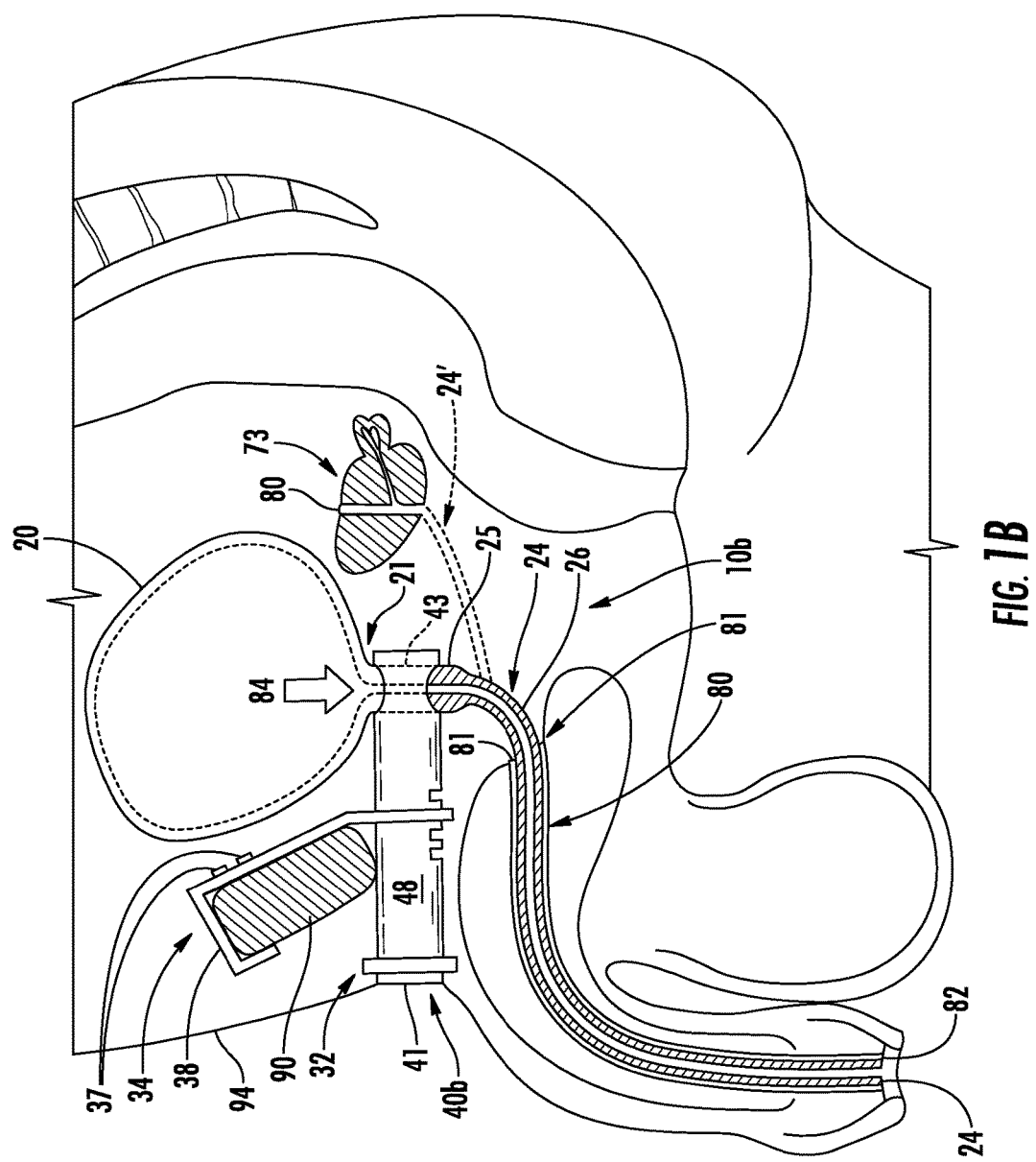

The structure, operation, and advantages of the present preferred embodiment of the invention will become further apparent upon consideration of the following description taken in conjunction with the accompanying drawings, wherein:

FIGS. 1A-1C are partial cross-sectional views of urinary flow control device embodiments of the invention that are implanted in human bodies according to method of the invention, wherein section hatching of the overall body is omitted for the sake of clarity.

FIGS. 1A and 1B show a pinch type of device embodiment implanted in a female and a male body, respectively, according to the invention.

FIG. 1C shows an occlusion type of device embodiment implanted in a male body, according to the invention.

Figure 2:
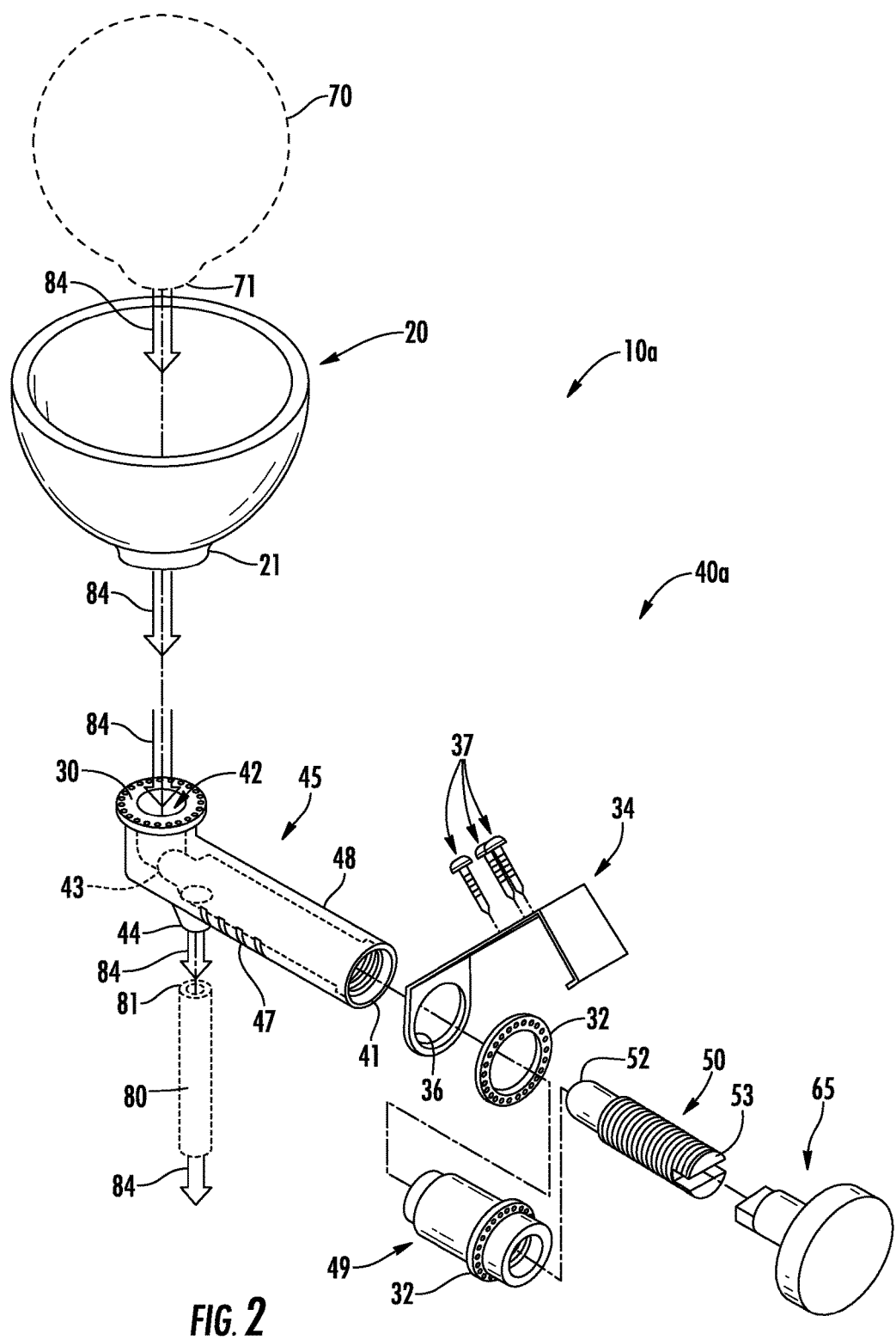

FIG. 2 is an exploded perspective view of the occlusion type of device, according to the invention.

Figure 3:
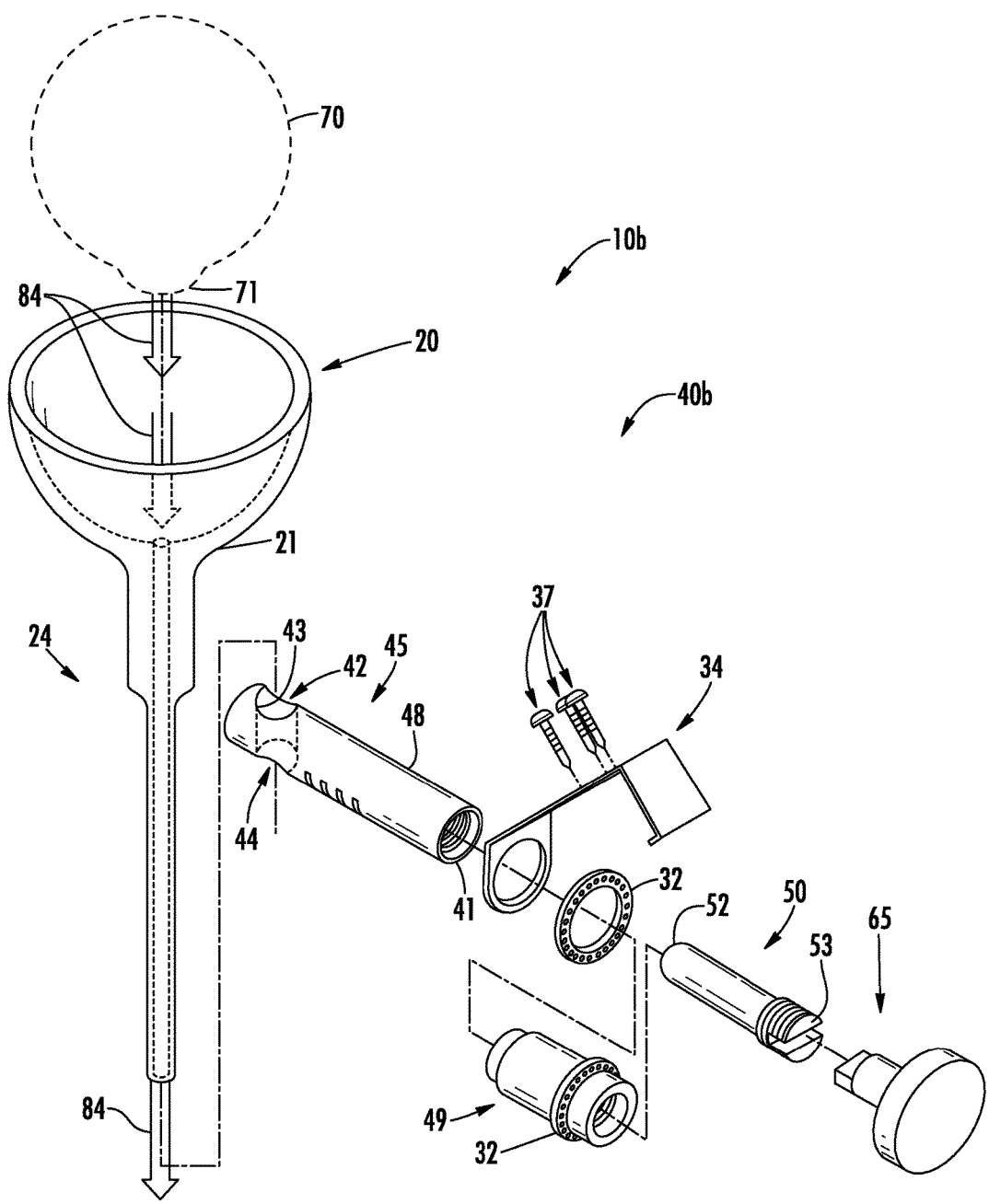

FIG. 3 is an exploded perspective view of the pinch type of device, according to the invention.

Figure 4A:
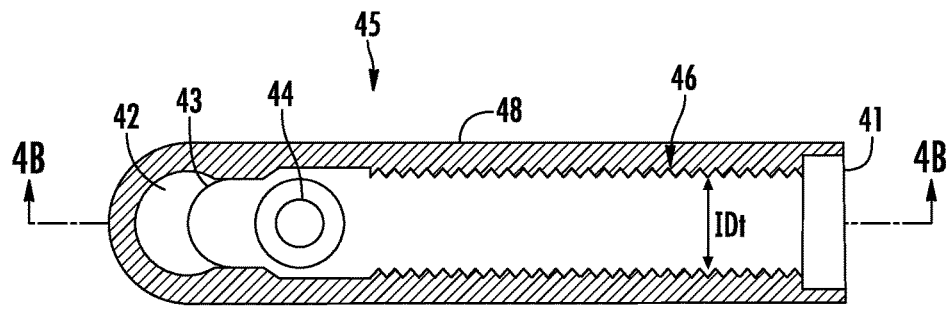
Figure 4B:
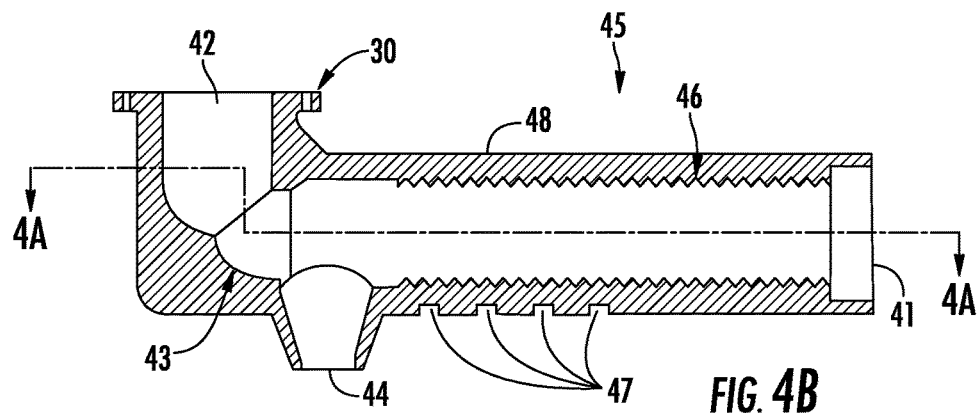

FIGS. 4A and 4B are top and side cross-sectional views, respectively, of an occlusion type valve housing, the sections being taken along the lines 4A-4A and 4B-4B, respectively, according to the invention.

Figure 4C:
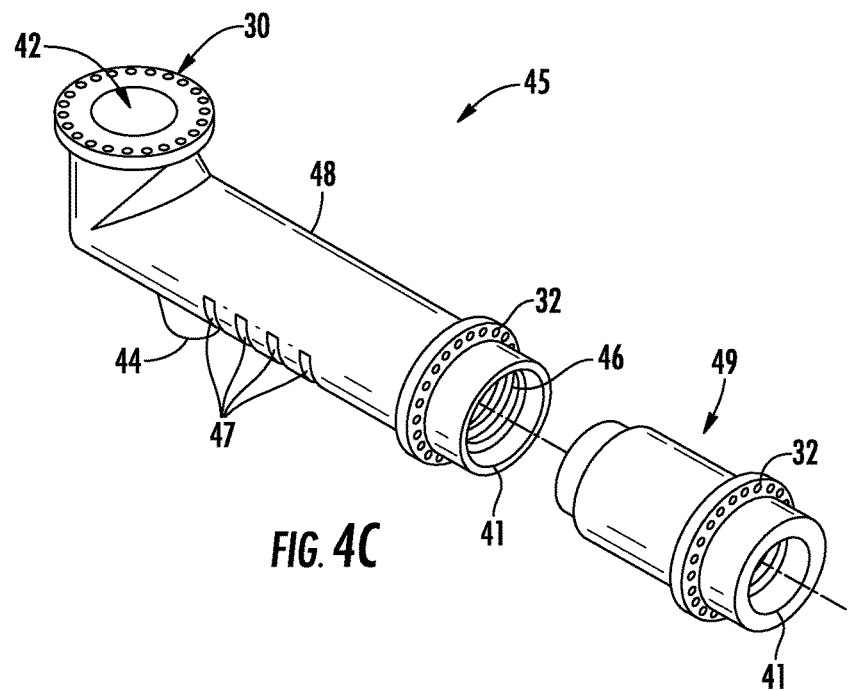

FIG. 4C is a perspective view of an occlusion type valve housing and an extender tube, according to the invention.

FIGS. 5A and 5B are side cross-sectional views of an occlusion type valve showing an actuator positioned, respectively, to open the valve, and to close the valve, according to the invention.

FIGS. 6A and 6D are combined as a perspective view of an occlusion type valve actuator, and a mating valve control tool, respectively, according to the invention.

FIG. 6B is a side view of an occlusion type valve actuator with an embodiment of a stopper shown rotated to an open, and a closed position, respectively, according to the invention.

FIG. 6C is a side view of an occlusion type valve actuator with another embodiment of a stopper shown rotated to an open, and a closed position, respectively, according to the invention.

Figure 7A:
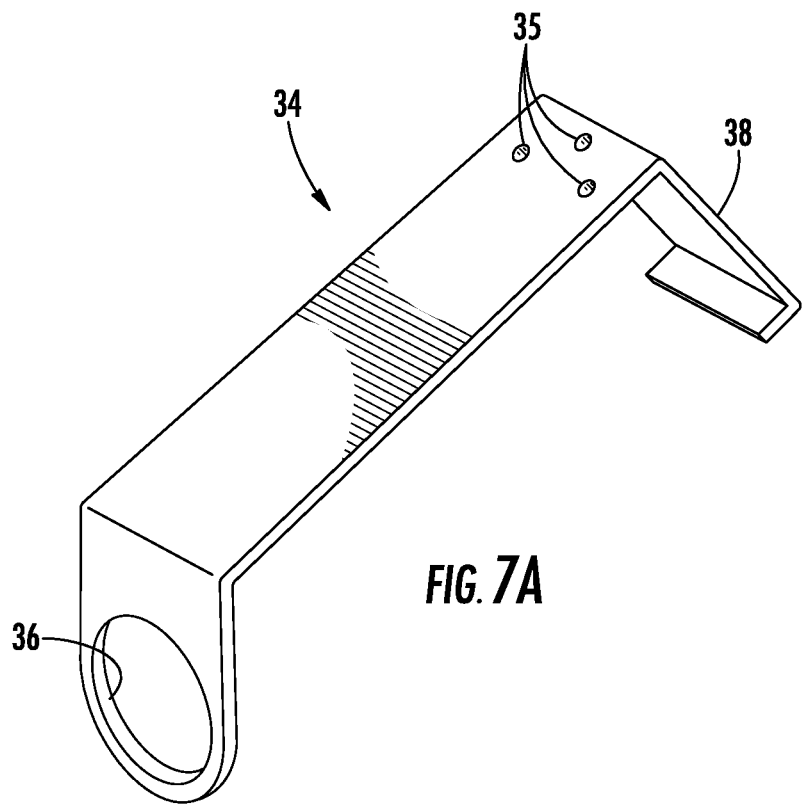
Figure 7B:
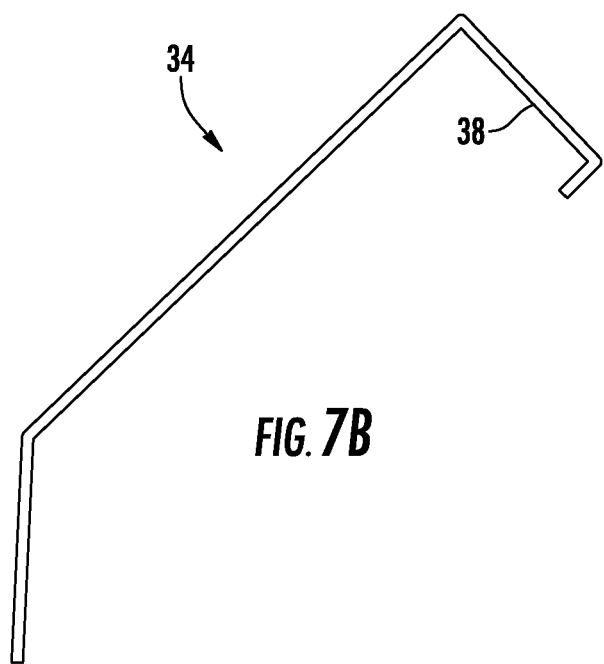

FIGS. 7A and 7B are a perspective view and a side view, respectively, of a valve hanger according to the invention.

FIGS. 8A, 8B and 8C are side cross-sectional views of a pinch type of device that has a first design of urine duct, and two different valve actuator/stopper embodiments, and showing an open valve and a closed valve in FIGS. 8B and 8C, respectively, according to the invention.

FIG. 8D is a top cross-sectional view (hatching omitted for clarity) of an upper portion compared to a lower portion of the first design of urine duct, according to the invention.

FIG. 8E is a side cross-sectional view of the pinch type of device that has a second design of urine duct, according to the invention.

FIG. 9A is a perspective view of a pinch type valve housing, according to the invention.

FIGS. 9B and 9C are side and top cross-sectional views, respectively, of a pinch type valve housing, the sections being taken along the lines 9B-9B and 9C-9C, respectively, shown in FIG. 9A, according to the invention.

FIG. 9D is a top cross-sectional view of the pinch type valve housing with the upper part of the first design of urine duct also shown in FIG. 8D, according to the invention.

FIGS. 10A-10E are side views of the pinch type valve actuator with different stopper embodiments, FIG. 10E also showing an end view of the FIG. E stopper, according to the invention.

FIG. 11 is a top cross-sectional view of a valve attached to the abdominal wall, particularly showing a spring biased embodiment of actuator driving mechanism adapted for non-contact control by a remote embodiment of the valve control tool, according to the invention.

Figure 12A:
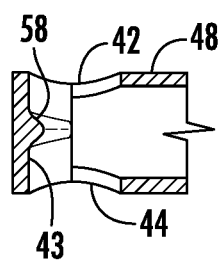
Figure 12B:
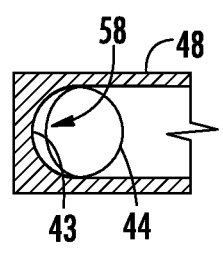
Figure 13A:
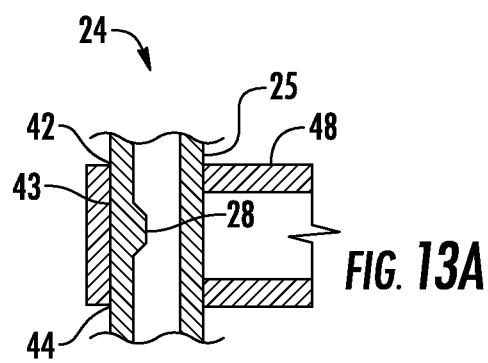
Figure 13C:
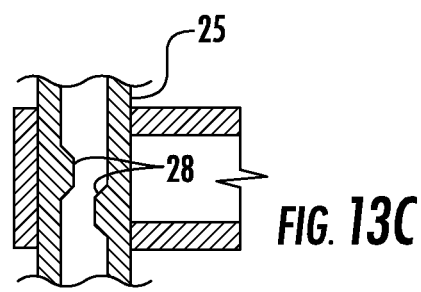
Figure 13B:
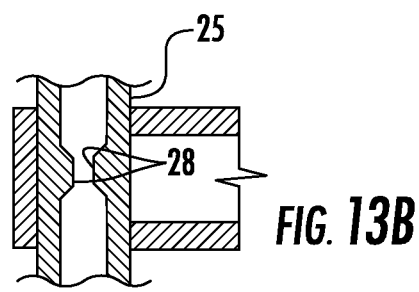
Figure 13D:
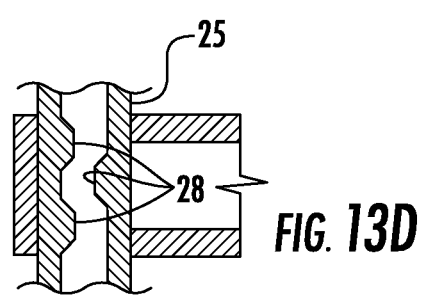

FIGS. 12A and 12B are side and top cross-sectional views, respectively, of a portion of a pinch type valve housing tube with a flow restriction bump built into the valve seat, according to the invention.

FIGS. 13A-13D are side cross-sectional views of a portion of a pinch type valve housing tube and urine duct, showing several embodiments of flow restriction bumps that are formed on the inside of the duct wall, according to the invention.

DETAILED DESCRIPTION OF THE INVENTION

The following table is a glossary particularly listing drawing reference numbers or symbols and associated names of elements, features and aspects of the invention(s) disclosed herein.

| REF. | TERMS AND DEFINITIONS |
|---|---|
| 10 | Urinary Flow Control Device - Major Embodiments:<br>10a = Occlusion type. Valve closure by blocking the flow. Valve closure parts are in contact with urine, i.e., within the urine flow channel 84.<br>10b = Pinch type. Valve closure by pinching closed the flow channel (contained by duct 24) |
| 20 | Bladder skirt. Biocompatible material may be formed into a cup-like anti-prolapse support, a patch/repair covering, a partial or a full artificial/replacement bladder |
| 21 | Neck/outlet opening of skirt. Supplements or replaces natural bladder neck/outlet 71 |
| 24 | Urine duct, artificial form of urine flow channel 84 (instead of urethra 80), for containing and conducting the urine flow |
| 25 | = upper (valve) portion, generally in the valve, adapted for pinch closing function. |
| 26 | = lower (urethral) portion, adapted to perform like a urethra, especially in the lower genitalia. |
| 28 | Flow restriction bump (restriction, break) formed inside the urine duct 24 |
| 30 | Inlet attachment ring (e.g., attaching valve to bladder), stitch ring, flange |
| 32 | Control portal attachment ring (e.g., attaching valve housing to abdominal wall), stitch ring, flange |
| 33 | Plug to seal closed the control portal 41. May be removable (e.g., gasket friction, screw threads), or fixed (e.g., adhesive, plastic weld). |
| 34 | Valve Hanger |
| 35 | Hanger attachment screw holes |
| 36 | Hanger Attachment Ring |
| 37 | Hanger Attachment Screws |
| 38 | Hanger Pelvic Hook |
| 40 | Valve (housing 45 with actuator 50). Flow control valve part of device 10<br>Major embodiments:<br>40a = Occlusion valve/occlusion type (valve stopper in flow channel directly blocks flow)<br>40b = Pinch valve/pinch type (indirect closing of flow channel by pinching duct 24 walls together) |
| 41 | Control portal, opening at distal end of valve housing 45, providing access into the housing tube 48 and thereby to any of: the valve internal components, the urine flow channel 84, the bladder, and the abdominal cavity (cutting and repair may be required). The housing tube 48 is generally attached at the abdominal wall, making the portal 41 either transcutaneous or subcutaneous. The portal may be sealed (e.g., plug 33), and/or may be configured as a transcutaneous "port". |

-continued

| REF. | TERMS AND DEFINITIONS |
|---|---|
| 42 | Valve Inlet |
| 43 | Valve Seat |
| | ---Note: "flow channel" 84 includes 42, 43, 44 (into, through, out of the valve) |
| | --The urine flow in/along the flow channel may be contained by the internal surfaces of the valve, or may be contained in a duct 24 that defines the flow channel through the valve. |
| 44 | Valve Outlet |
| 45 | Valve Housing (comprises at least 41, 42, 43, 44, 48; and optionally 46, 47). Also may have any of attachments such as 30, 32, 33, 34, 49, 68. |
| 46 | Internal threads of valve housing tube 48 (mating with actuator threads 56), the housing part of a screw type embodiment of actuator driving mechanism 60. |
| 47 | Hanger Positioning Grooves |
| 48 | Housing Tube, longitudinally extending, tubular portion of housing used to hold actuator |
| 49 | Extender Tube (optional to add length to tube 48) |
| 50 | Valve Actuator (stem 51 + stopper 52 + control head 53) |
| 51 | Actuator Stem |
| 52 | Stopper of Valve, on proximal end of actuator/stem, engages with valve seat 43 to stop flow through the valve. Example embodiments/shapes include: |
| | 52a = dome (generally hemispherical) |
| | 52b = dome with cutout passage/aperture 57a (e.g., a half dome). (for occlusion type valve) |
| | 52c = aligned-orifice stopper (orifice is passage/aperture 57b) (for occlusion type valve) |
| | 52d = separate ball (so that rotating actuator stem doesn't rotate the stopper) |
| | 52e = pivoting dome (another way to prevent stopper rotation. Dome is on a pivoting connection to stem) |
| | 52f = pivoting bar (transverse bar on a pivoting connection to stem). Preferably with edges/ends rounded for engagement with the valve seat. (for pinch type valve) |
| 53 | Control Head (distal end of actuator) |
| 54 | Tool Receiving End of actuator 50 (e.g., Slot for blade 66; e.g., an active tip = steel or magnetic tip for attraction to magnetic control tool tip 66) |
| 55 | Shoulder on actuator stem 51, e.g., for limiting longitudinal movement of actuator 50 by engaging with insert 68 and/or spring 69. |
| 56 | Screw Threads on actuator stem 51 (mating with housing threads 46), the actuator part of a screw type of actuator driving mechanism. |
| 57 | Flow Passage (aperture) through an occlusion type valve stopper 52: |
| | 57a = cutout |
| | 57b = orifice |
| 58 | Flow Restriction Bump (protrusion, restriction, break) formed on a valve seat 43 |
| 60 | Actuator driving mechanism, Drive, Driver. Apparatus associated with the valve actuator/stem to cause/control/enable opening and closing of the valve by operationally moving the valve actuator 50 in the valve housing tube 48. Has a mechanical or remote (non-contact) controller 65, plus associated enabling components (e.g., 46, 54, 55, 56, 66, 68, 69) |
| 65 | Controller or control tool. Separate/External device for elective user controlling of valve operation. (FIG. 6D shows a mechanical embodiment, and FIG. 11 shows a non-contact (remote) embodiment that could be used without removing a portal plug 33, and/or through the skin for a sealed, subcutaneous control portal 41) |
| 66 | Control Tool Tip (e.g., blade on a mechanical control tool 65; e.g., magnet on remote-acting control tool 65; e.g., transmitter/antenna for electronic remote controller 65) |
| 68 | Housing Tube Insert; e.g., positioned in the tube 48 by screw thread engagement, optional part of the actuator driving mechanism 60 (FIGS. 6C, 11) |
| | Embodiments include: a screw-in collar, bushing or plug as a backstop for spring or to limit actuator movement; a solenoid; a motor, etc. |
| 69 | Spring, optional part of the actuator driving mechanism 60. Example in FIG. 11 shows it on actuator stem 51 to bias the position/movement of actuator 50 (and stopper 52). Can be used in both pinch type and occlusion type valves. |
| | An example in FIG. 11 shows compression spring between insert/collar 68 and shoulder 55 on stem. Spring holds valve "normally closed" until controller pulls the actuator outward to disengage the stopper from the valve seat. |
| | Environmental Elements/Body Parts |
| 70 | Bladder |
| 71 | Bladder Neck, including bladder outlet opening where proximal end 81 of the urethra 80 normally connects (embedded in prostate of males) |
| 73 | Prostate (Male) |
| 80 | Urethra (natural urine flow channel), portion of the urinary tract below the bladder |
| 81 | Proximal end of urethra (closest to bladder, inlet opening of urethra) |
| 82 | Urethral meatus (natural urine outlet opening at distal end of urethra) |
| 84 | Urine Flow Channel, generic term for natural or artificial conduit/flow path for urine passing from location of bladder to the urine outlet opening. Normally this is the urethra 80 connected between bladder neck 71 and urethral meatus 82. For the urinary flow control device, at least a portion of the channel is directed through a control valve 40 and may be contained in an artificial urine duct 24. The reference number 84 may also be applied to the urine flow itself, as will be clear from the context of use and the arrow indicators so labeled in the drawings. |

-continued

| REF. | TERMS AND DEFINITIONS |
|---|---|
| 90 | Pubic Symphysis |
| 94 | Abdominal Wall (thickness not illustrated) |

The invention(s) will now be described with reference to the drawings and using reference numbers and symbols listed with term definitions in the above table.

Example embodiment(s) of the hereindisclosed inventive urinary flow control device 10 for repairing urinary incontinence is illustrated in various views in the Figures, and may be generally referred to herein as a flow control device, control device, or simply device. Also, the device 10 may be referred to as a flow control valve 40 (or simply valve) according to the main function of the device 10. Variations in term use should be interpreted according to the context in which they are used.

The urinary flow control device 10 is a surgically implantable system of artificial components that work together to repair or replace any or all of the interrelated components (body parts), and their functions, of a natural lower urinary tract including the bladder 70 down to the urinary meatus 82. We use the term "artificial" to mean manufactured from biocompatible materials suitable for implanting, preferably for long term (substantially "permanent") use in the body. The device 10 is designed to be particularly suitable for a method of implementation and use as described herein.

It will be seen that the present invention(s) include at least one, and sometimes several different embodiments of artificial body part repair/replacement components, some of which are optional to enable selection of the optimum solution for a particular patient, each patient/user having their own particular circumstances to accommodate.

For example, a bladder skirt 20 may be adapted to patch/repair bladder conditions ranging from supporting a prolapsing bladder 70 (as in FIG. 1A), to patching a partially removed bladder wall (e.g., due to cancer surgery), all the way to completely replacing a removed bladder (as in FIG. 1B). The bladder skirt 20 is preferably manufactured as a complete enclosure that may be cut if or as needed according to the surgeon's judgment at the time of implantation. If the bladder 70 is substantially intact, is self supporting and only needing incontinence control then the skirt 20 may be omitted.

FIG. 1C illustrates an embodiment 10a of an artificial flow control device 10 (also see FIG. 2) where an embodiment 40a of control valve 40 is implanted without a bladder skirt 20 (and using the existing bladder 70 and urethra 80). FIG. 2 shows that a skirt 20 may optionally be implanted as a component of the device 10a. The valve 40a has a valve inlet 42 that is attached to the existing bladder neck 71 (e.g., by stitching through the holes around an inlet attachment ring 30) such that a urine flow path/channel 84 out of the bladder 70 (and/or 20) is directed into a housing tube 48 of the valve 10a and down to a valve seat 43 that the user can electively control to be closed or open (FIG. 5B or 5A, respectively) by operationally moving an actuator 50 to sealingly engage or disengage, respectively, a valve stopper 52 on the actuator 50 with the valve seat 43. When engaged, generally by direct contact of stopper and valve seat surfaces, the stopper 52 substantially blocks the passage for urine flow 84, therefor we call this embodiment of valve 40 an occlusion type of valve 40a, which comprises the valve component of an occlusion type of flow control device 10a.

When the occlusion valve 40a is opened (electively by the user) the urine flow 84 passes through the valve seat 43 and out through a valve outlet 44 where it re-enters the natural urine conduit (urethra 80) which is attached to the outlet 44 by conventional fasteners such as, for example, adhesive, stitching and/or a wrapped silicone rubber membrane.

It may be noted in FIG. 1C (and also 1B) that for valve implanting in a male patient it is generally necessary to remove the prostate 73 from the bladder, for reasons including, for example, the prostate is too spongy to hold stitches for attaching to the valve; it cannot be wrapped in a membrane because it swells as men age; and it may take up too much room to allow addition of the valve 10. In FIG. 1C it has been removed from the body. FIG. 1B shows an optional alternative wherein it is moved out of the way but kept functional by cauterizing the open end of the severed urethra 80, and then connecting the seminal vesicles to the urine conduit 84 (labeled 80 or 24) by adding an extra conduit 24' (e.g., a piece of artificial duct 24). FIGS. 1A and 1B show another flow control device embodiment 10b in two different implanting situations. This embodiment is a pinch type of device 10b shown more completely in FIG. 3. Particularly the FIGS. 8A-8C show that the "pinch type" label is due to the device 10b comprising a pinch type valve 40b, wherein the urine flow channel 84 is an artificial duct 24 for containing and conducting the urine flow through the control valve 40b between the valve seat 43 and the stopper 52, and urine flow is stopped by engagement of the stopper 52 with the valve seat 43 such that the urine duct 24 between them is pinched closed. The user can electively control the pinch valve 40b to be closed or open (FIG. 8C or 8B, respectively) by operationally moving the actuator 50 to engage or disengage, respectively, a valve stopper 52 on the actuator 50 with the valve seat 43. When the pinch valve 40b is opened (electively by the user) the urine in the duct 24 is allowed to flow through the valve seat 43 and down into a lower portion 26 of the duct 24 which conducts the flow 84 through the genital region and out to the urethral meatus 82.

Besides the male/female differences, FIGS. 1A-1B show two different bladder treatments using the bladder skirt 20: in FIG. 1A for supplementing the bladder 70 as a support and/or as a repair/patch (e.g., when the bladder neck 71 and/or sphincter muscles are damaged or removed); and in FIG. 1B as a complete replacement for a removed bladder 70. The skirt 20 is recommended for male patients because removing the prostate 73 damages or at least weakens even a healthy bladder neck 71.

Among the many advantages of the pinch type of flow control device 10b is that it provides a complete solution for urinary tract problems by optionally replacing all of the natural components with functionally equivalent (or better) artificial components that are capable of eliminating incontinence problems. In other words, the bladder 70 with sphincter valves, and the complete urine flow channel 84 (urethral tract 80 out to the meatus 82) may be replaced by surgically implanted bladder skirt/replacement 20, valve 40b, and urine duct 24 out to the meatus 82.

Referring to FIGS. 3 and 8A-8E the pinch type of urinary flow control device 10b includes a preferably unitary combined bladder skirt 20 and specially configured two part urine duct 24, plus a pinch type of flow control valve 40b that has the valve seat 43 positioned on one side of a straight through passage from inlet 42 to outlet 44. The valve housing 45 is otherwise similar to the occlusion type housing 45 and functions according to substantially the same principles: i.e., an operationally moveable valve actuator 50 extends longitudinally within the housing 45 (i.e., the tube 48 part of it), and comprises a stem 51 with a stopper 52 at the valve seat end, and an actuator driving mechanism 60 is associated with it. One difference is that the pinch valve actuator 50 must move the stopper 52 longitudinally to operate the valve, whereas the occlusion valve actuator 50 can also operate by axially rotating the stopper 52 in the valve seat if a compatible stopper design is used (e.g., the cutout dome stopper 52b and the aligned orifice stopper 52c).

The urine duct 24 is hollow, and begins where it is flowingly connected to the bladder skirt 20 at the skirt neck 21 with its bladder outlet opening. An upper, valve portion 25 of the duct extends the urine flow channel 84 from the bladder outlet opening through the control valve 40, and a lower, urethral portion 26 continues the urine flow channel to the urine outlet opening (preferably the urethral meatus 82).

The lower duct 26 is made from a biocompatible material that is sufficiently thin, flexible, stretchable and durable for permanently implanting within a final portion of the natural urethra 80 and for attaching at the urethral meatus 82. It can be seen in FIGS. 1A-1B that the final portion of the urethra 80 is generally grown into the surrounding tissue as shown. The duct material will typically also be fused to the surrounding tissue (inside of the urethra) due to ingrowth or the like. Particularly for the male patient, this means that the lower duct 26 must be able to accommodate significant stretching when the penis is moved and/or experiences erection. Consequently a preferred embodiment is silicone rubber tubing that has 100-800% elongation, and is much less stiff than catheters are, which must be rigid enough to enable being pushed up through the urethra into the bladder 70. Our lower duct 26 tubing will not have rigidity as wall thickness is significantly lower. For example maybe French size 9 having 0.062" ID and 0.125" OD (⅛ inch) as shown in FIG. 8D. A method for attaching the lower duct 26 is to sleeve it inside the natural urethra 80 and let extra length hang beyond the meatus 82; the surgeon will cut off excess tubing after tissue ingrowth has occurred. Alternatively attach it by conventional means at the meatus 82 and ingrowth will take care of the rest.

The upper duct 25 (the valve portion) extends through the valve from inlet 42 to outlet 44. It is a much tougher type of silicone rubber such that it will withstand years of pinch-closing cycles. It may be thick walled, as shown in FIGS. 8A-8D, or may be a larger OD with a relatively thin wall, as in FIG. 8E (variant embodiment referenced as duct 24' and upper portion 25'). Test results will help determine the optimum.

The tubing durability will also be affected by the nature of the pinch action, which is determined by factors such as shown in FIGS. 8A-13D, including: stopper shape and relationship to the valve seat shape; rotation of the stopper against the tubing surface likely should be avoided (for example using non-rotating stoppers 52d, 52e, 52f, e.g., FIGS. 10C-10E, 11). The same factors also affect pinch closing effectiveness and ease.

FIGS. 12A-13D show varying valve seat 43 shapes and tubing ID shapes of the duct 24 upper portion 25 wherein flow restriction bumps 58 and 28, respectively, are provided for adjusting flow control.

The following comprises an outline that summarizes important aspects of this disclosure.

Common Aspects Of Valves 40 (FIGS. 1A-3, 6A, 6D, 7A-7B, 6C and 11):

valve housing 45 with flow channel 84 from inlet 42 (located proximal to bladder neck 71) through valve seat 43 and out of outlet 44.

a single housing tube 48 extends from inlet 42 and valve seat 43 to a control portal/opening 41 at a distal end located at the abdominal wall 94 (under or through the skin)

valve actuator 50 in the tube 48 has a stopper 52, stem 51, and control head 53 stopper 52 engages/disengages with valve seat 43 to stop or allow urine flow actuator driving mechanism (drive) 60 controls movement of actuator 50 in the tube 48 to operate the valve 40 under control of a mechanical or remote/non-contact controller (external valve control tool) 65. (see FIGS. 6A, 6C, 6D, 11) The drive 60 has elements that cause rotational and/or longitudinal movement of stem 51 and its associated stopper 52. Drive elements may include any of:

mating screw threads 46 and 56, actuator's tool receiving end 54, engaging with control tool tip 66 an insert 68 which may be, for example: a remote controlled solenoid coil or other electric device like a micro motor or a piezoelectric driver.

a ferrous or magnetic actuator tool receiving end 54 and a spring 69 configured such that the actuator 50 is operationally moved in response to a proximally placed ferrous or magnetic remote control tool tip 66.

stem shoulder 55 engages with insert 68 to limit or stop longitudinal movement of actuator 50. A spring 69 may be added to bias the position of actuator 50. Example in FIG. 11 shows compression spring 69 between collar-like insert 68 and shoulder 55 on stem 51. Spring holds valve closed until controller 65 pulls the actuator 50 outward to disengage the stopper 52 from the valve seat 43.

mechanical controller 65 (FIG. 6D)=physical, direct contact, hand manipulated tool 65 embodiment with a control tip 66 that physically (mechanically) engages with an actuator tool receiving end 54 at the control head 53 on the actuator stem 51 (e.g., FIG. 6A). Example is a male "screwdriver" tip (66), (e.g., a blade, Philips, hex/Allen wrench tip) which has a handle to hold/turn it after it is inserted through the control portal 41 and into a corresponding female "screw head" (tool receiving end 54).

remote controller 65 (FIG. 11)=a non-contact or remote acting tool 65 embodiment that could be used through a plug 33 or the skin 94 (dashed line), i.e., with a sealed subcutaneous control portal 41. Examples:

controller 65 is electronic: e.g., radio remote control, Bluetooth and/or smart phone, and control "tip" 66 is a transmitter/antenna; or non-electronic but remote-acting control tool 65: e.g., magnet control tip 66 that attracts or repels the actuator control receiver 54, or for example closes a magnetic reed switch in an electrical actuator driving mechanism 60.

holding/attachment elements (FIGS. 1A-3, 4C, 7A-7B, 11): stitch rings 30, 32 (either integral to housing or attached during implantation operation), tube extension(s) 49 as needed, hanger 34 with screws 37 and attachment ring 36, and grooves 47 in housing tube bladder skirt 20 (support, replacement, attachment means, etc.) (FIGS. 1A-1B, 2, 3, 8A)

The Two Major Embodiments, And Advantages Of Pinch Vs. Occlusion Type (It may be noted that the pinch type flow control device 10b (with pinch type valve 40b) is the most developed and improved version):

Occlusion Type 10a, 40a, (FIGS. 1C, 2, 4A-6C):
 how it is implanted, (connected between/to urethra 80 and bladder neck 71, optionally with skirt 20)
 valve seat 43 & stopper embodiments (52a-52f)
 modes of operation:
  linear/longitudinal move in/out, with or without rotation (FIGS. 5A-5B),
  rotate in place (FIG. 6C, optionally with a spring between insert 68 and shoulder 55 to hold stopper 52 (e.g., 52b, 52c) tight in the valve seat 43)

Pinch Type 10b, 40b (Preferred Embodiment) (FIGS. 1A, 1B, 3, 8A-13D):
 how it is implanted: urine duct 24 replaces natural urethra 80 from bladder 70 to urinary meatus 82, passing inside of urethra 80 as needed (e.g., in penis). This contains the urine flow channel 84 in a completely sealed duct. Bladder 70 is supported or replaced by a skirt 20 having a neck 21 connected to the bladder neck 71. Skirt 20 is integral with urine duct 24.
 urine duct 24 has a durable (e.g., thick walled) upper part 25 that passes straight through the valve housing 45 (inlet opening 42, valve seat 43, outlet opening 44)
 remainder 26 of urine duct 24 is thin and flexible, suitable for sleeving inside natural urethral passage 80 where it is integrated with surrounding tissue such as in penis.
 valve seat 43 (FIGS. 9A-9D) and stopper 52 embodiments (e.g., 52a, d, e, f; FIGS. 10A-10E),
 modes of operation: linear/longitudinal move in/out, with or without rotation (e.g., FIGS. 8B-8C, using screw threads, or FIG. 11 with collar 68 and spring 69 against shoulder 55),
 optional valve seat variations:
  (FIGS. 12A-12B) break/protrusion 58 on valve seat 43 modifies valve seat shape.
  (FIGS. 13A-13D) restriction bump 28 in valve (upper) portion 25 of the urine duct 24.
 Other Notes:

When the urinary flow control device 10 is used with a bladder 70 or a collapsible artificial equivalent (e.g., FIG. 1b skirt 20 formed as a bladder replacement), no venting is necessary, however, a vent could be added, if required for any reason.

The physical dimensions and construction of the urinary flow control device 10 is selected by the physician based on the sex of the patient as well as other anatomical and medical considerations. The anatomical placement of the urinary flow control device 10 is illustrated in FIGS. 1A-1C and 11. The urinary flow control device 10 is also surrounded by a biocompatible material such as SILASTIC® membrane or the like in order to prevent abdominal erosions by keeping the valve 40 makeup or construction materials away from internal peritoneal tissues and organs. Different sizes of the valve 40 of the urinary flow control device 10 may be provided so that the doctor can select the optimal fit with the individual patient. The valve 40 is positioned to securely anchor the top portion of the valve inlet 42 of the housing 45 into place at the bottom of the bladder neck 71 otherwise known as the trigone region of the bladder 70. The position of the optional anti-prolapse skirt 20 may be lower or higher on the trigone region depending upon the individual's anatomy and the surgeon's discretion. The optional anti-prolapse skirt 20 can be attached to the bladder by stitching the skirt 20 into place using fasteners which include biodegradable sutures, staples, stitching, adhesives, or other means for fastening. For the occlusion type valve 40a, a biocompatible material may be inserted between the housing 45 at the valve outlet 44 and the urethra 80 wherein the biocompatible material provides a tubular extension connector to the urethra. An optional embodiment of the biocompatible material provides a tubular extended protrusion through the existing natural urethra in lieu of an interface anastomosis. Regardless of the attachment of the urethra 80, the occlusion type flow control device 10a provides a flow channel 84 from the bladder 70 to the urethra 80, with the valve 40a providing an obstruction in the urine flow channel 84 to prevent fluid from entering the urethra 80 unless the valve 40 is in the opened position.

Referring to FIGS. 1A-1C and 7A-7B, the tube 48 extends from the valve inlet 42 near the bladder 70, under, by, through, or around the pubic symphysis 90, with a vertical stabilization device (valve hanger) 34 hooked 38 over, and attached (e.g., using screws 37 in screw holes 35) to the pelvic girdle near the pubic symphysis 90 or superior rami. The pubic symphysis 90 is the midline cartilaginous joint uniting the superior rami of the left and right pubic bones. As the pubic symphysis 90 is a cartilage material, it can optionally be slit or drilled or otherwise used to provide a harness for the housing tube 48. The cartilage material will regenerate and grow to help repair and fill in any gaps provided by the implantation operation. Referring also to FIGS. 2-3 and 7A-7B, the hanger 34 has an attachment ring 36 for sliding onto the valve housing tube 48 to be secured in interlocking hanger positioning grooves 47.

The placement of the valve 40 in this location allows the patient/user to have easy access to the valve actuator control head 53, and also minimizes the noticeability of the portal 41 as it is generally below the waistline of clothing, and high enough as to not prevent sexual activity of the patient nor interfere with the nerve bundle called the clitoris in the female. In addition, the portal 41 location is low enough on the body that if the patient gains weight, the weight will generally be gained above the portal 41. If for any reason the housing tube 48 is, or becomes too short, e.g., pregnancy or severe weight gain, etc., the tube 48 can be extended with one or more extender tubes 49 (as shown in FIGS. 2, 3, and 4c).

It is contemplated that the valve housing 45 may be comprised of stainless steel (e.g., ss3161), nickel-titanium shape memory alloy (e.g., NITINOL®), carbon fiber, plastics such as PEKK, or any other biocompatible material capable of providing support for the valve's 40 main features. For example, in one embodiment, the valve 40 may be constructed from a biocompatible metal material, and in another embodiment the valve 40 may be constructed from a polymer material optimized in shape and additionally surrounded by a biocompatible material. The portions of the valve 40 exposed to urine (only in occlusion type valve 40a) must be composed of a material resistant to urinary system environment. It is further contemplated that a SILASTIC® membrane manufactured by Dow Corning or any other biocompatible material such as GORE-TEX® by W. L. Gore and DACRON® by DuPont, or other biomaterials such as polyurethane, polydimethylsiloxane, cellulose, biologic tissue engineered matrix and other silicone polymer membranes, can be applied over the valve 40 and also may be used to enclose the valve 40. In addition to preventing urethral erosion from contact of tissue with urine, the biocompatible material over the valve 40 may help create a more stable, stronger support for the valve 40, and bladder 70 (and anti-prolapse skirt 20 if present), which when integrated with the body, will help decrease healing time, and decrease infection potential. Additionally, valve 40 may have a coating of a drug delivery membrane. This drug coating will provide delivery of drugs over a period of time and will permit for faster healing and integration with the body at a lower rate of infection potential.

A skirt 20 with integral duct 24 is used to attach the pinch valve device 10*b* to the bladder 70, and an inlet attachment ring 30 is used to attach the occlusion valve device 10*a* to the bladder 70, optionally having an intermediary skirt 20 as shown in FIG. 2.

After the valve 40 is attached to the bladder 70, the patient or care-giver may operate the device to control the flow of urine. FIGS. 5A-5B and 8B-8C illustrate opening and closing the valves, granting the individual to control "on-demand" urination.

An actuator driving mechanism 60 closes and opens the valve by respectively moving the stopper 52 into or out from engagement with the valve seat 43.

Driving mechanism 60 embodiments: valve housing tube 48 contains a housing portion 46 of an actuator drive mechanism such as, for example, internal threads 46 that mate with an actuator portion 56 of the actuator driving mechanism, for example screw threads 56 on the actuator stem 51.

The valve 40 may be fully opened by removing the valve actuator 50 (e.g., using the control tool 65 to unscrew the actuator 50 in the retracting/opening direction). If the actuator 50 is not functioning properly, the valve actuator 50 can be completely removed from housing tube 48 and replaced with a new valve actuator 50. At least for the occlusion type valve 40*a*: with the actuator 50 removed, the control portal 41 then becomes an optional flow channel to be used for urinary diversion, to drain urine, or a temporary catheter can be inserted into the bladder 70 above the valve inlet 42.

Actuator Driving Mechanism 60 Variations–Mechanical Or Remote: Valve actuator 50 can be moved between an open position and a closed position via a tool 65 (e.g., FIGS. 6D, 11) that may be directly in contact with the valve mechanism (e.g., actuator control head 53 in FIG. 6A), as well as by hands free operation or remotely (without directly contacting the valve mechanism) via "remote control", (e.g., controller 65 in FIG. 11, which may be, for example: a hand held controller, like a TV remote control, a radio (e.g., Bluetooth) smart phone/computer controller application, an electric or magnetic attraction/repulsion device, or the like).

Referring to FIGS. 6B-6C, the occlusion valve stopper 52 configuration may be modified to have an aperture 57 strategically located in the valve stopper 52 to permit a quarter turn to open the valve by positioning the aperture 57 to bypass the stopper 52 (around it with the cutout stopper 52*b*, or through it with the orifice stopper 52*c*) while it remains seated in the valve seat 43.

Given the present description of example valve seat 43 and stopper 52 designs, many variations may be apparent to one of ordinary skill in fluid valve design arts, all of which are considered to be within the scope of the invention if suitable for implementation with a valve actuator 50 operating within a valve housing tube 48 as described.

Although the invention has been illustrated and described in detail in the drawings and foregoing description, the same is to be considered as illustrative and not restrictive in character—it being understood that the embodiments shown and described have been selected as representative examples including presently preferred embodiments plus others indicative of the nature of changes and modifications that come within the spirit of the invention(s) being disclosed and within the scope of invention(s) as claimed in this and any other applications that incorporate relevant portions of the present disclosure for support of those claims. Undoubtedly, other "variations" based on the teachings set forth herein will occur to one having ordinary skill in the art to which the present invention most nearly pertains, and such variations are intended to be within the scope of the present disclosure and of any claims to invention supported by said disclosure.

What is claimed is:

1. An implantable urinary flow control device for elective user control of urinary function in a male or female patient's body, the device comprising:
    an artificial urine duct adapted for containing and conducting urine flow;
    an implantable pinch valve for stopping the urine flow through the artificial urine duct; and
    a separate external valve control tool;
    wherein the pinch valve and the artificial urine duct are adapted for implantation in a urine flow channel that conducts urine from a bladder to a urine outlet opening of the body, the pinch valve comprising:
        a generally tubular, longitudinally extending valve housing comprising a valve seat at a proximal end, and a control portal at a distal end; and
        an operationally moveable valve actuator extending longitudinally within the valve housing, the valve actuator comprising an elongated rigid stem with a stopper at a proximal valve seat end of the stem, and an actuator driving mechanism associated therewith;
    wherein the artificial urine duct passes through the pinch valve between the valve seat and the stopper; and
    wherein the external valve control tool is adapted to operationally engage with the actuator driving mechanism for elective user control of operational movement of the valve actuator between open and closed positions, wherein the closed position prevents urine flow through the artificial urine duct by pinching the artificial urine duct closed through engagement of the stopper with the valve seat, and the open position allows urine to flow through the artificial urine duct by disengaging the stopper.

2. The implantable urinary flow control device of claim 1, further comprising:
    a hanger adapted to be attached to the body's pubic symphysis for anchoring the valve housing when implanted in the body.

3. The implantable urinary flow control device of claim 1, wherein:
    the control portal is adapted to be attached at the body's abdominal wall such that the actuator driving mechanism is enabled for operational engagement with the external valve control tool.

4. The implantable urinary flow control device of claim 3, wherein:
    attachment of the control portal provides a portal opening through the abdominal wall such that a tip of the external valve control tool tip is insertable for mechanical engagement with a tool receiving end of the actuator driving mechanism.

5. The implantable urinary flow control device of claim 3, wherein:
attachment of the control portal is subcutaneous such that the external valve control tool utilizes non-contact remote engagement with the actuator driving mechanism.

6. The implantable urinary flow control device of claim 1, wherein the actuator driving mechanism comprises:
mating screw threads on the stem and inside of the valve housing such that turning the stem advances or retracts the stopper relative to the valve seat.

7. The implantable urinary flow control device of claim 1, wherein the actuator driving mechanism comprises:
an insert comprising an electromotive device connected for operationally moving the valve actuator in response to engagement by the external valve control tool.

8. The implantable urinary flow control device of claim 1, wherein the actuator driving mechanism comprises:
a ferrous or magnetic tool receiving end and a spring configured such that the actuator is operationally moved in response to a proximally placed ferrous or magnetic tip of the external valve control tool.

9. The implantable urinary flow control device of claim 1, further comprising:
an artificial support skirt adapted to supportingly cup at least a portion of the bladder around a bladder neck outlet, the skirt comprising a neck and an outlet opening adapted for flowing connection to the bladder neck outlet.

10. The implantable urinary flow control device of claim 9 wherein the skirt is adapted to completely enclose or replace the bladder.

11. The implantable urinary flow control device of claim 9 wherein the skirt comprises an artificial patch or supplement to a damaged bladder, a bladder construct, a tissue engineered neoplast, or a synthetic bladder construct.

12. The implantable urinary flow control device of claim 1, wherein the artificial urine duct comprises:
an artificial bladder skirt comprising a neck with an outlet opening;
an upper, valve portion of the duct adapted to extend the urine flow channel from the skirt's outlet opening through the pinch valve; and
a lower, urethral portion of the duct adapted to continue the urine flow channel to the body's urine outlet opening.

13. The implantable urinary flow control device of claim 12, wherein:
the lower urethral portion is adapted to be flowingly connected at a distal end to the body's natural urethra.

14. The implantable urinary flow control device of claim 12, wherein:
the lower urethral portion is adapted to be permanently implanted within a final portion of the body's natural urethra and is adapted to be flowingly connected at the body's urethral meatus.

* * * * *